(12) United States Patent
Canessa et al.

(10) Patent No.: US 8,799,221 B2
(45) Date of Patent: Aug. 5, 2014

(54) SHARED ARCHIVES IN INTERCONNECTED CONTENT-ADDRESSABLE STORAGE SYSTEMS

(76) Inventors: John Canessa, Apple Valley, MN (US); Kenneth Wright, Chino Hills, CA (US)

(*) Notice: Subject to any disclaimer, the term of this patent is extended or adjusted under 35 U.S.C. 154(b) by 0 days.

(21) Appl. No.: 13/092,243

(22) Filed: Apr. 22, 2011

(65) Prior Publication Data

US 2011/0320469 A1    Dec. 29, 2011

Related U.S. Application Data

(60) Provisional application No. 61/327,556, filed on Apr. 23, 2010.

(51) Int. Cl.
G06F 17/30 (2006.01)
G06F 17/00 (2006.01)
G06F 15/16 (2006.01)

(52) U.S. Cl.
CPC ...................................... G06F 17/30 (2013.01)
USPC ........... 707/638; 707/661; 707/696; 707/747; 707/793; 713/165; 711/108; 711/122; 709/213; 709/218

(58) Field of Classification Search
CPC .... G06F 17/3028; G06F 19/321; G06F 15/16
USPC .......... 707/638, 661, 696, 747, 793; 713/165; 711/108, 122; 709/213, 218
See application file for complete search history.

(56) References Cited

U.S. PATENT DOCUMENTS

| | | | |
|---|---|---|---|
| 4,149,239 A | 4/1979 | Jenkins et al. | |
| 4,491,725 A | 1/1985 | Pritchard | |
| 4,852,570 A | 8/1989 | Levine | |
| 4,860,112 A | 8/1989 | Nichols et al. | |
| 4,874,935 A | 10/1989 | Younger | |
| 4,945,410 A | 7/1990 | Walling | |

(Continued)

FOREIGN PATENT DOCUMENTS

| | | |
|---|---|---|
| DE | 19802572 | 5/1999 |
| EP | 0684565 | 11/1995 |

(Continued)

OTHER PUBLICATIONS

Bitcache, drupal.org, 2 pages.
European Response to the Communication Pursuant to Rule 161(1) and 162 EPC, dated May 13, 2011.
Ferelli, Mark, Content-addressable storage—Storage as I See it, Computer Technology Review, http://findarticles.com/p/articles/mi_m0BRZ/is_10_22/ai_98977101/, Oct. 2002, in 2 pages.

(Continued)

Primary Examiner — Yicun Wu
(74) Attorney, Agent, or Firm — Knobbe Martens Olson & Bear LLP

(57) ABSTRACT

Some of the embodiments herein provide a seamless cloud of storage. This storage may be content-addressable storage. An end application may or may not be exposed to the fact that content-addressable storage is used. Various embodiments herein provide event notification, which may allow applications or users to subscribe to particular events (such as storage of an X-ray by a particular entity). Some embodiments provide for a shared archive. A shared archive may provide homogeneous access to medical data, etc. that was previously stored into the CAS cloud by heterogeneous applications, varied data types, etc. Additionally, embodiments herein allow for the creation and distribution of virtual packages. For example, a user may create a virtual package for all images related to a patient so that she may have a virtual package of all of her medical data to present to a referring physician.

20 Claims, 13 Drawing Sheets

(56) References Cited

U.S. PATENT DOCUMENTS

| | | |
|---|---|---|
| 4,958,283 A | 9/1990 | Tawara et al. |
| 5,002,062 A | 3/1991 | Suzuki |
| 5,005,126 A | 4/1991 | Haskin |
| 5,019,975 A | 5/1991 | Mukai |
| 5,208,802 A | 5/1993 | Suzuki |
| 5,235,510 A | 8/1993 | Yamada et al. |
| 5,272,625 A | 12/1993 | Nishihara et al. |
| 5,291,399 A | 3/1994 | Chaco |
| 5,319,543 A | 6/1994 | Wilhelm |
| 5,319,629 A | 6/1994 | Henshaw et al. |
| 5,321,520 A | 6/1994 | Inga et al. |
| 5,321,681 A | 6/1994 | Ramsay et al. |
| 5,384,643 A | 1/1995 | Inga et al. |
| 5,410,676 A | 4/1995 | Huang et al. |
| 5,416,602 A | 5/1995 | Inga et al. |
| 5,451,763 A | 9/1995 | Pickett et al. |
| 5,469,353 A | 11/1995 | Pinsky et al. |
| 5,499,293 A | 3/1996 | Behram et al. |
| 5,513,101 A | 4/1996 | Pinsky et al. |
| 5,531,227 A | 7/1996 | Schneider |
| 5,542,768 A | 8/1996 | Rother et al. |
| 5,544,649 A | 8/1996 | David et al. |
| 5,586,262 A | 12/1996 | Komatsu et al. |
| 5,597,182 A | 1/1997 | Reber et al. |
| 5,597,995 A | 1/1997 | Williams et al. |
| 5,605,153 A | 2/1997 | Fujioka et al. |
| 5,655,084 A | 8/1997 | Pinsky et al. |
| 5,659,741 A | 8/1997 | Eberhardt |
| 5,671,353 A | 9/1997 | Tian et al. |
| 5,687,717 A | 11/1997 | Halpern et al. |
| 5,721,825 A | 2/1998 | Lawson et al. |
| 5,724,582 A | 3/1998 | Pelanek et al. |
| 5,734,629 A | 3/1998 | Lee et al. |
| 5,734,915 A | 3/1998 | Roewer |
| 5,763,862 A | 6/1998 | Jachimowicz et al. |
| 5,796,862 A | 8/1998 | Pawlicki et al. |
| 5,809,243 A | 9/1998 | Rostoker et al. |
| 5,822,544 A | 10/1998 | Chaco et al. |
| 5,823,948 A | 10/1998 | Ross et al. |
| 5,832,488 A | 11/1998 | Eberhardt |
| 5,848,198 A | 12/1998 | Penn |
| 5,848,435 A | 12/1998 | Brant et al. |
| 5,859,628 A | 1/1999 | Ross et al. |
| 5,867,795 A | 2/1999 | Novis et al. |
| 5,867,821 A | 2/1999 | Ballantyne et al. |
| 5,869,163 A | 2/1999 | Smith et al. |
| 5,873,824 A | 2/1999 | Doi et al. |
| 5,882,555 A | 3/1999 | Rohde et al. |
| 5,884,271 A | 3/1999 | Pitroda |
| 5,899,998 A | 5/1999 | McGauley et al. |
| 5,909,551 A | 6/1999 | Tahara et al. |
| 5,911,687 A | 6/1999 | Sato et al. |
| 5,914,918 A | 6/1999 | Lee et al. |
| 5,924,074 A | 7/1999 | Evans |
| 5,942,165 A | 8/1999 | Sabatini |
| 5,946,276 A | 8/1999 | Ridges |
| 5,950,207 A | 9/1999 | Mortimore |
| 5,982,736 A | 11/1999 | Pierson |
| 5,995,077 A | 11/1999 | Wilcox |
| 5,995,345 A | 11/1999 | Overbo |
| 5,995,965 A | 11/1999 | Experton |
| 6,006,191 A | 12/1999 | DiRienzo |
| 6,014,629 A | 1/2000 | Debruin-Ashton |
| 6,021,404 A | 2/2000 | Moukheibir |
| 6,022,315 A | 2/2000 | Iliff |
| 6,032,120 A | 2/2000 | Rock et al. |
| 6,035,280 A | 3/2000 | Christensen |
| 6,041,703 A | 3/2000 | Salisbury et al. |
| 6,067,075 A | 5/2000 | Pelanek |
| 6,131,090 A | 10/2000 | Basso, Jr. et al. |
| 6,148,331 A | 11/2000 | Parry |
| 6,149,440 A | 11/2000 | Clark et al. |
| 6,155,409 A | 12/2000 | Hettinger |
| 6,241,668 B1 | 6/2001 | Herzog |
| 6,260,021 B1 | 7/2001 | Wong |
| 6,272,470 B1 | 8/2001 | Teshima |
| 6,278,999 B1 | 8/2001 | Knapp |
| 6,283,761 B1 | 9/2001 | Joao |
| 6,363,392 B1 | 3/2002 | Halstead et al. |
| 6,397,224 B1 | 5/2002 | Zubeldia et al. |
| 6,415,295 B1 | 7/2002 | Feinberg |
| 6,421,650 B1 | 7/2002 | Goetz |
| 6,564,256 B1 | 5/2003 | Tanaka |
| 6,591,242 B1 | 7/2003 | Karp |
| 6,671,714 B1 | 12/2003 | Weyer et al. |
| 6,934,698 B2 | 8/2005 | Judd |
| 6,954,802 B2 | 10/2005 | Sutherland et al. |
| 6,976,165 B1 * | 12/2005 | Carpentier et al. .......... 713/165 |
| 7,162,571 B2 | 1/2007 | Kilian et al. |
| 7,213,022 B2 | 5/2007 | Whelan et |
| 7,240,150 B1 | 7/2007 | Todd et al. |
| 7,266,556 B1 | 9/2007 | Coates |
| 7,283,857 B1 * | 10/2007 | Fallon et al. ................ 600/407 |
| 7,298,836 B2 | 11/2007 | Wellons |
| 7,366,836 B1 | 4/2008 | Todd et al. |
| 7,379,605 B1 | 5/2008 | Ticsa |
| 7,398,391 B2 | 7/2008 | Carpentier et al. |
| 7,415,731 B2 | 8/2008 | Carpentier et al. |
| 7,428,611 B1 | 9/2008 | Todd et al. |
| 7,434,057 B2 | 10/2008 | Yagawa |
| 7,475,432 B2 | 1/2009 | Carpentier et al. |
| 7,487,551 B2 | 2/2009 | Carpentier et al. |
| 7,523,489 B2 | 4/2009 | Bossemeyer et al. |
| 7,530,115 B2 | 5/2009 | Carpentier et al. |
| 7,539,813 B1 | 5/2009 | Todd et al. |
| 7,546,486 B2 | 6/2009 | Slik et al. |
| 7,552,340 B2 | 6/2009 | Ooi et al. |
| 7,552,356 B1 | 6/2009 | Waterhouse et al. |
| 7,590,672 B2 | 9/2009 | Slik et al. |
| 7,591,022 B2 | 9/2009 | Carpentier et al. |
| 7,593,720 B2 | 9/2009 | Moon et al. |
| 7,621,445 B2 | 11/2009 | Esseiva et al. |
| 7,640,271 B2 | 12/2009 | Logan, Jr. |
| 7,657,581 B2 | 2/2010 | Orenstein et al. |
| 7,694,331 B2 | 4/2010 | Vesikivi et al. |
| 7,734,603 B1 | 6/2010 | McManis et al. |
| 7,783,608 B2 * | 8/2010 | Shitomi .................. 707/667 |
| 7,797,546 B2 | 9/2010 | Kenson |
| 7,802,087 B2 | 9/2010 | Gatto et al. |
| 7,836,493 B2 | 11/2010 | Xia et al. |
| 8,036,513 B2 | 10/2011 | Oashi et al. |
| 8,045,214 B2 | 10/2011 | Samari |
| 8,059,304 B2 | 11/2011 | Samari |
| 8,233,777 B2 | 7/2012 | Seo |
| 8,281,391 B2 * | 10/2012 | Yamada et al. .................. 726/21 |
| 2001/0027402 A1 | 10/2001 | Ramsaroop |
| 2002/0010679 A1 | 1/2002 | Felsher |
| 2002/0083030 A1 | 6/2002 | Yang et al. |
| 2002/0085476 A1 | 7/2002 | Samari-Kermani |
| 2002/0103675 A1 | 8/2002 | Vanelli |
| 2002/0103811 A1 | 8/2002 | Fankhauser et al. |
| 2002/0138524 A1 | 9/2002 | Ingle et al. |
| 2003/0005464 A1 | 1/2003 | Gropper et al. |
| 2003/0040940 A1 | 2/2003 | Nehammer |
| 2003/0220822 A1 | 11/2003 | Fiala et al. |
| 2004/0006492 A1 | 1/2004 | Watanabe |
| 2004/0078236 A1 | 4/2004 | Stoodley et al. |
| 2004/0083123 A1 | 4/2004 | Kim et al. |
| 2004/0107210 A1 | 6/2004 | Yang et al. |
| 2004/0146272 A1 | 7/2004 | Kessel et al. |
| 2004/0187012 A1 | 9/2004 | Kohiyama et al. |
| 2004/0187027 A1 | 9/2004 | Chan |
| 2004/0199762 A1 | 10/2004 | Carlson et al. |
| 2004/0210458 A1 | 10/2004 | Evans et al. |
| 2005/0075909 A1 | 4/2005 | Flagstad |
| 2005/0086082 A1 | 4/2005 | Braunstein et al. |
| 2005/0125252 A1 | 6/2005 | Schoenberg et al. |
| 2005/0125254 A1 | 6/2005 | Schoenberg |
| 2005/0125258 A1 | 6/2005 | Yellin et al. |
| 2005/0144172 A1 | 6/2005 | Kilian et al. |
| 2005/0192837 A1 | 9/2005 | Fears et al. |
| 2005/0197859 A1 | 9/2005 | Wilson et al. |
| 2005/0267863 A1 | 12/2005 | Carpentier et al. |
| 2006/0080307 A1 | 4/2006 | Carpentier et al. |

(56) References Cited

U.S. PATENT DOCUMENTS

| | | |
|---|---|---|
| 2006/0085226 A1 | 4/2006 | Kamber |
| 2006/0155584 A1 | 7/2006 | Aggarwal |
| 2006/0164930 A1 | 7/2006 | Seo et al. |
| 2006/0179112 A1 | 8/2006 | Weyer et al. |
| 2006/0242144 A1 | 10/2006 | Esham et al. |
| 2007/0027715 A1 | 2/2007 | Gropper |
| 2007/0061170 A1 | 3/2007 | Lorsch |
| 2007/0073776 A1 | 3/2007 | Kalalian et al. |
| 2007/0180509 A1 | 8/2007 | Swartz et al. |
| 2008/0005030 A1 | 1/2008 | Schlarb et al. |
| 2008/0013365 A1 | 1/2008 | Yueh |
| 2008/0031601 A1 | 2/2008 | Hashimoto et al. |
| 2008/0065718 A1 | 3/2008 | Todd et al. |
| 2008/0071577 A1 | 3/2008 | Highley |
| 2008/0104099 A1 | 5/2008 | Walczak et al. |
| 2008/0183719 A1 | 7/2008 | Kageyama et al. |
| 2008/0208919 A1 | 8/2008 | i Dalfo et al. |
| 2008/0222654 A1 | 9/2008 | Xu et al. |
| 2008/0244196 A1 | 10/2008 | Shitomi et al. |
| 2008/0274687 A1 | 11/2008 | Roberts et al. |
| 2008/0285759 A1 | 11/2008 | Shaw |
| 2008/0313236 A1 | 12/2008 | Vijayakumar et al. |
| 2008/0319798 A1 | 12/2008 | Kelley |
| 2009/0043828 A1 | 2/2009 | Shitomi |
| 2009/0055924 A1 | 2/2009 | Trotter |
| 2009/0070834 A1 | 3/2009 | Limbasia |
| 2009/0089335 A1 | 4/2009 | Shitomi et al. |
| 2009/0119764 A1 | 5/2009 | Applewhite et al. |
| 2009/0132775 A1 | 5/2009 | Otani et al. |
| 2009/0133013 A1 | 5/2009 | Criddle et al. |
| 2009/0157987 A1 | 6/2009 | Barley et al. |
| 2009/0198515 A1 | 8/2009 | Sawhney |
| 2009/0204433 A1 | 8/2009 | Darian et al. |
| 2009/0219411 A1 | 9/2009 | Marman et al. |
| 2009/0228520 A1 | 9/2009 | Yahata et al. |
| 2009/0240764 A1 | 9/2009 | Peleg et al. |
| 2009/0252480 A1 | 10/2009 | Wright et al. |
| 2009/0319736 A1 | 12/2009 | Otani et al. |
| 2010/0046747 A1 | 2/2010 | Oashi et al. |
| 2010/0061702 A1 | 3/2010 | Tanaka et al. |
| 2010/0138446 A1 | 6/2010 | Canessa et al. |
| 2010/0174750 A1 | 7/2010 | Donovan et al. |
| 2010/0185502 A1 | 7/2010 | Roberts et al. |
| 2010/0286997 A1 | 11/2010 | Srinivasan |
| 2011/0231837 A1 | 9/2011 | Sheehan et al. |
| 2012/0151436 A1 | 6/2012 | Ahadian et al. |

FOREIGN PATENT DOCUMENTS

| | | |
|---|---|---|
| EP | 0781032 | 6/1997 |
| EP | 0952726 | 10/1999 |
| GB | 2096440 | 10/1982 |

OTHER PUBLICATIONS

Menezes A et al.: "Handbook of Applied Cryptography, Key Management Techniques" Handbook of Applied Cryptography, Jan. 1, 1996, pp. 543-590.

HoneyComb Fixed Content Storage, Solaris, http://hub.opensolaris.org/bin/view/Project+honeycomb/Webhome, Oct. 26, 2009 in 2 pages.

International Search Report and Written Opinion issued in PCT/US2009/054799, dated Nov. 16, 2009.

International Search Report and Written Opinion issued in PCT/US2009/061890, dated Dec. 10, 2009.

International Search Report and Written Opinion issued in PCT/US2011/063987, dated Sep. 6, 2012.

Mellor, Chris, Making a Hash of File Content, Techworld, http://features.techworld.com/storage/235/making-a-hash-of-file-content/?, Dec. 3, 2009, in 2 pages.

Quinlan, S., et al., Venti: a new approach to archival storage, doc.cat-v.org/plan_9/4th_edition/papers/venti, in 20 pages.

Rhea, S., et al., Fast, Inexpensive Content-Addressed Storage in Foundation, http://doc.cat-v.org/plan_9/misc/foundation/, in 22 pages.

Fintan J McEvoy et al.: "Security of Patient and Study Data Associated with DICOM Images when Transferred Using Compact Disc Media" Journal of Digital Imaging; The Journal of the Society for Computer Applications in Radiology, vol. 22, No. 1, Aug. 21, 2007 (pp. 65-70).

Tolia, N., et al., Opportunistic Use of Content Addressable Storage for Distributed File Systems, USENIX Association, Jun. 9, 2003, in 15 pages.

Twisted Storage, http://twistedstorage.sourceforge.net/index.html, in 7 pages.

Twisted Storage, http://twistedstorage.sourceforge.net/news.html, in 1 page.

Medical Imaging Magazine, Jan. 2000. Product Showcase, Automated Dicom Exchange Station. 1 page.

Terry May Titled "Medical Information Security: the Evolving Challenege" copyright 1998 IEEE doc #0-7803-4535-5/98 pp. 85-92.

Ted Cooper Titled "Kaiser Permanente Anticipates High Cost as it Gears up for HIPAA" IT Health Care Strategist vol. 1, No. 10 Oct. 1999 p. 4.

Haufe G. et al.: PACS at Work: A Multimedia E-Mail Tool for the Integration of Voices and Dynamic Annotation, Computer Assisted Radiology, Proceedings of the International Symposium, 1998 Etsevier Science B.V., pp. 417-420.

Dimitroff D C et al: "An Object Oriented Approach to Automating Patient Medical Records" Proceedings of the International Computer Software and Applications Conference. (Compsac), US, Washington, IEEE. Comp. Soc. Press, vol. CONF. 14, 1990, pp. 82-87.

Kleinholz L et al: "Multimedia and PACS. Setting the Platform for Improved and New Medical Services in Hospitals and Regions" Car '96 Computer Assisted Radiology. Proceedings of the International Symposium on Computer and Communication Systems for Image Guided Diagnosis and Therapy, Paris, France, Jun. 1996, pp. 313-322, XP002083080 1996, Amsterdam, Netherlands, Elsevier, Netherlands, ISBN: 0-444-82497-9.

1996 Annual HIMSS Conference and Exhibition, Managing Care: The Race Is On, dated Mar. 3-7, 1996.

FilmX Presentation Slides.

Candelis website excerpt, http://www.candelis.com via the Internet Wayback Machine (Archive.org), Jul. 19, 2010.

Carestream website excerpt, http://carestreamhealth.com via the Internet Wayback Machine (Archive.org), Nov. 20, 2010.

eMix website excerpt, http://www.emix.com via the Internet Wayback Machine (Archive.org), Jul. 10, 2011.

GE Healthcare IT website excerpt, http://www.dynamic-imaging.com via the Internet Wayback Machine (Archive.org), Jan. 27, 2010.

HeartIT website excerpt, http://heartit.com via the Internet Wayback Machine (Archive.org), Jan. 29, 2009.

Infinitt North America website excerpt, http://infinittna.com via the Internet Wayback Machine (Archive.org), Feb. 28, 2009.

InSite One website excerpt, http://www.insiteone.com via the Internet Wayback Machine (Archive.org), Aug. 8, 2010.

lifeIMAGE website excerpt, http://www.lifeimage.com via the Internet Wayback Machine (Archive.org), Nov. 4, 2010.

McKesson website excerpt, http://www.mckesson.com via the Internet Wayback Machine (Archive.org), Oct. 20, 2010.

MyMedicalRecords.com website excerpt, http://www.mymedicalrecords.com via the Internet Wayback Machine (Archive.org), Aug. 1, 2010.

PACS Image website excerpt, http://www.pacsimage.com via the Internet Wayback Machine (Archive.org), Apr. 2, 2010.

ScImage website excerpt, http://www.scimage.com via the Internet Wayback Machine (Archive.org), Sep. 27, 2010.

See My Radiology website excerpt, http://www.seemyradiology.com via the Internet Wayback Machine (Archive.org), Jul. 11, 2010.

Symantec Health Press Release, http://www.symantec.com/about/news/release/article.jsp?prid=20100819_01, Aug. 19, 2010.

Xrayline website excerpt, http://www.xrayline.com via the Internet Wayback Machine (Archive.org), Oct. 13, 2010.

International Search Report issued in PCT/US2011/033647, dated Nov. 28, 2011.

\* cited by examiner

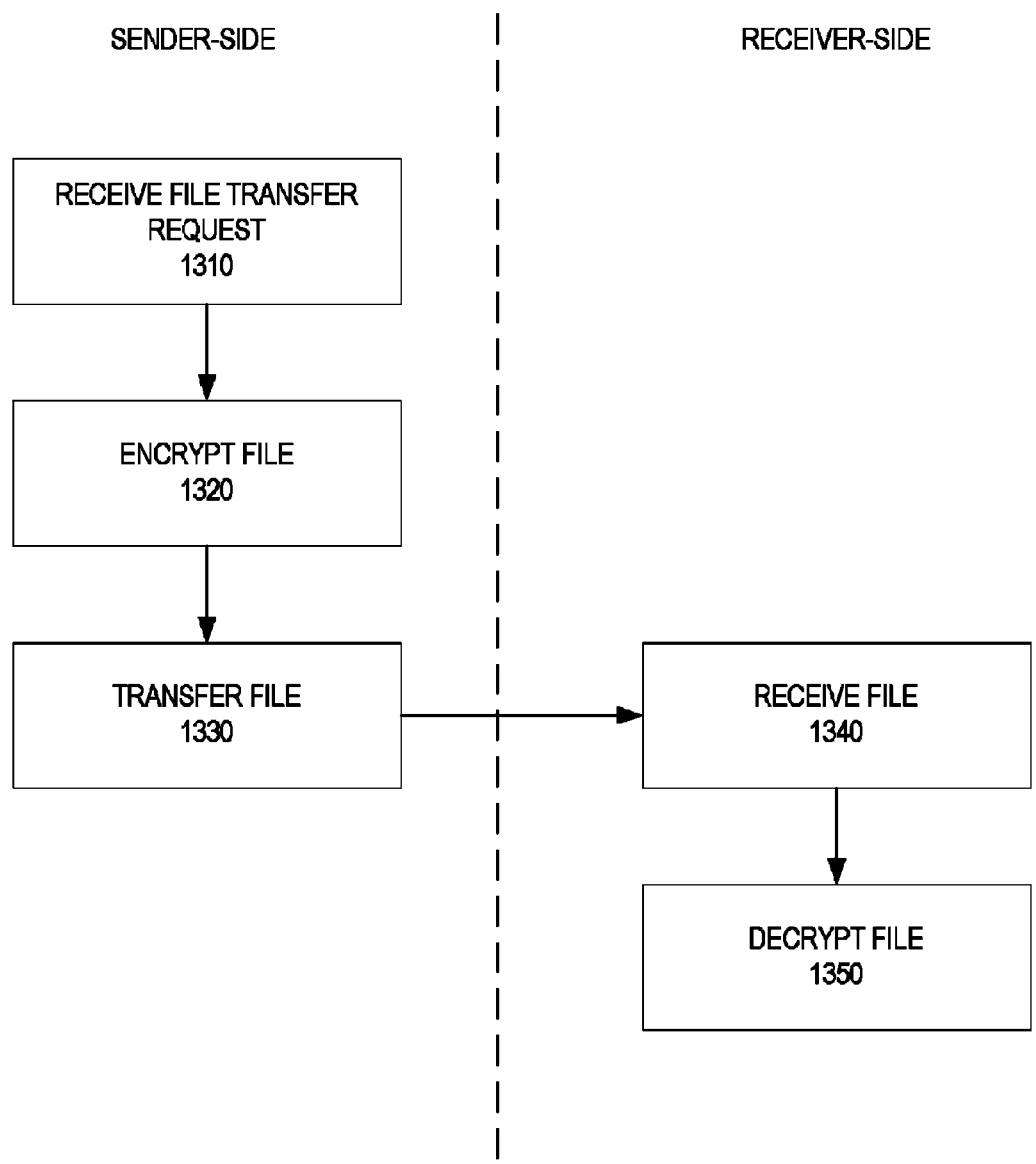

SHARED ARCHIVES IN INTERCONNECTED CONTENT-ADDRESSABLE STORAGE SYSTEMS

CROSS-REFERENCE TO RELATED APPLICATIONS

This application claims the benefit of U.S. Provisional Application No. 61/327,556, entitled Management of Interconnected Content-Addressable Storage Systems, filed Apr. 23, 2010, which is incorporated by reference herein in its entirety for all purposes. This application also incorporates by reference in their entirety for all purposes U.S. application Ser. No. 13/092,243, filed concurrently herewith, entitled "Event Notification in Interconnected Content-Addressable Storage Systems" to John Canessa et al. and U.S. application Ser. No. 13/092,229, filed concurrently herewith, entitled "Management of Virtual Packages of Medical Data in Interconnected Content-Addressable Storage Systems" to John Canessa et al.

FIELD

This disclosure relates to content-addressable storage (CAS) for handling, storing, and distributing medical imaging information and, more specifically, to shared archives in interconnected content-addressable storage systems.

BACKGROUND

Many files stored in computer systems contain data that is not expected to change over time. In some systems, the percentage of files that are expected to remain unchanged can range up to 90% of all of the stored files. Examples of data and files that are expected to remain unchanged include medical images, images of cancelled bank checks, images collected by oil and gas exploration, surveillance videos, files containing television news clips, and many types of archival and historical data. Other files are expected to change regularly, such as a database file, a word processing document that is being edited, and any type of file that represents current state, such as a file holding cumulative email messages as they arrive.

Stored files must be accessible. Further, they must be accessible whether it's the kind of data that changes quickly, such as a file storing current email, or whether it is the kind of data that will not change much over time, such as medical images. CAS technology can be used to store different types of data including, by way of example, data that does not change over time. Generally, a "handle" (not necessarily the location of the file in a directory) or a GUID (globally unique identifier) is created for each stored object. This handle can be created based on known techniques, such as hashing.

Current storage systems have a number of issues. The options for production of groupings of files may be limited. Another issue with current systems is that the heterogeneous storage of data (e.g., but a number of different medical imagers and reporting systems), can make accessing stored data difficult—both because of the distributed nature of the storage and because of the heterogeneous nature of the storage of the data.

These and other issues are addressed by the embodiments described herein. Some embodiments address one or more of these issues, while others address a different subset of issues.

SUMMARY

Embodiments of the systems, methods, and devices described herein overcome problems of the prior art and enable management of interconnected content-addressable storage systems.

Some embodiments include receiving a first indication (e.g., a request) to store a first file containing first medical data and first related metadata in a content-addressable storage cloud from a first computer-implemented application. The metadata related to the first file is parsed to produce first information. The first file is stored in the content-addressable storage cloud —and a first identifier for locating the stored first file is received. The first information and first identifier are then stored in a shared archive. A second indication to store a second file containing second medical data and second related metadata in the content-addressable storage cloud is received from a second computer-implemented application. The second related metadata of the second file is parsed to produce second information. The second file is stored in the content-addressable storage cloud and a second identifier for locating the stored second file is received. The second information and second identifier are stored in the shared archive. At some point a first query is received from a requestor for a first data item and related data from the shared archive. When the first information satisfies the first query related to the first data item and the second information fails to satisfy the first query related to the first data item, a second data item may be determined based at least in part on the first data item, wherein the first data item and the second data item are distinct—and a second query may be performed for the second data item. When the first information satisfies the first query related to the first data item and the second information satisfies the second query related to the second data item, a response may be sent to the requestor of the first query with information related to the first file and the second file. In some embodiments, the second data item may be determined based on the first file and/or a master index. Responding to the query may include responding with the first identifier and/or the first file. The responses to queries and/or the execution of queries may be controlled by access control permissions for the requestor. Numerous other embodiments are described herein.

These and other features and advantages of embodiments will become apparent from the following description of embodiments. Neither this summary nor the following detailed description purports to define the invention.

BRIEF DESCRIPTION OF THE DRAWINGS

These and other features will now be described with reference to the drawings summarized below. These drawings and the associated description are provided to illustrate specific embodiments, and not to limit the scope of the invention.

FIG. 13 is a block diagram representing an exemplary process for encryption in a system of interconnected content-addressable storage systems.

DETAILED DESCRIPTION

Overview

Figure 1:
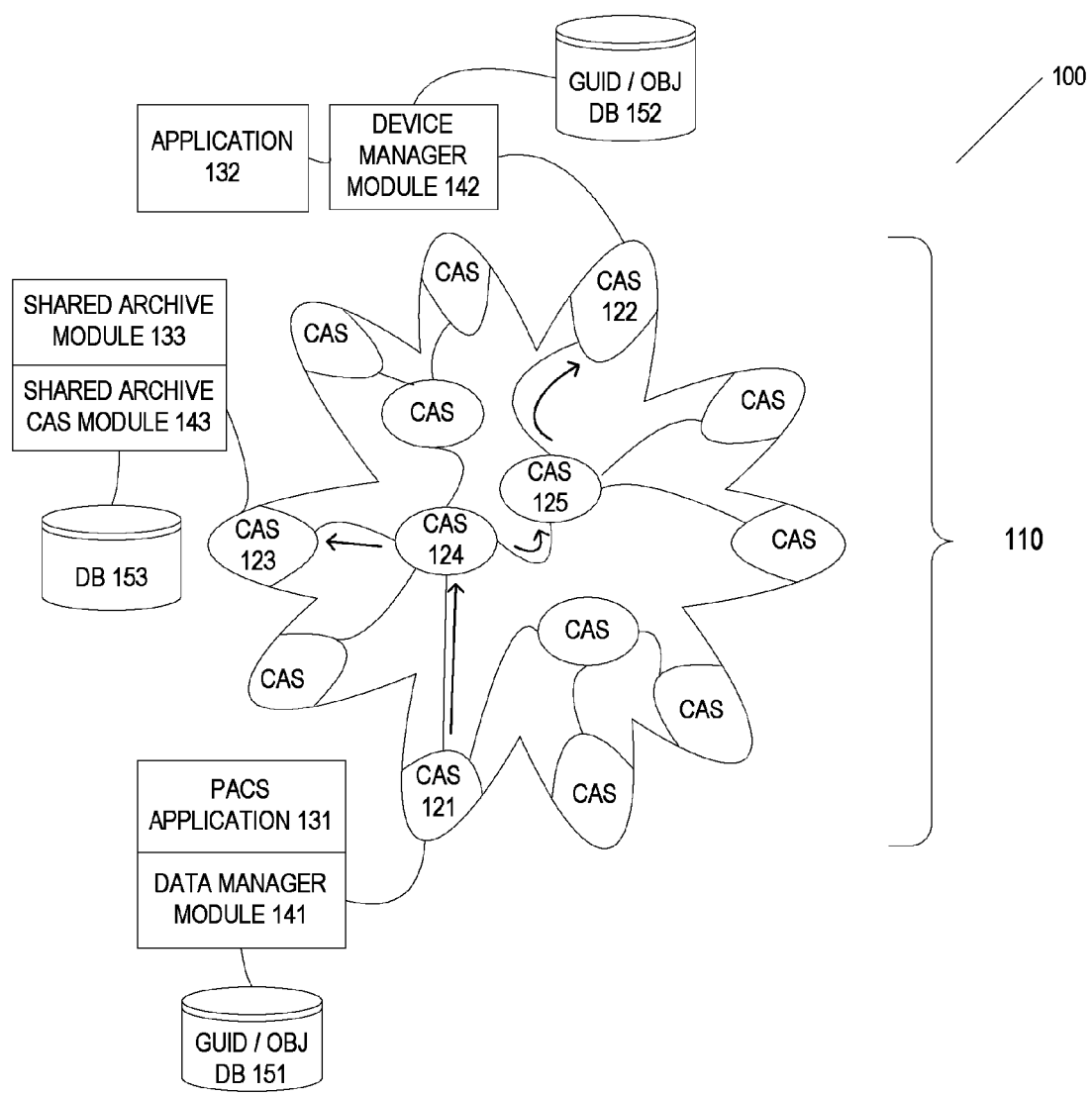
FIG. 1 illustrates a block diagram of an exemplary embodiment of a system for management of interconnected content-addressable storage systems.

In the following detailed description, references are made to the accompanying drawings that illustrate specific embodiments in which embodiments may be practiced. Electrical, mechanical, programmatic, and structural changes may be made to the embodiments without departing from the spirit and scope of the disclosure. The following detailed description is, therefore, not to be taken in a limiting sense and the scope of the disclosure is defined by the appended claims and their equivalents.

Various embodiments overcome one or more issues with the prior art. Other embodiments may overcome different issues with the prior art. For example, some embodiments overcome issues related to event notification, others: virtual packages, yet others: shared archives. Some embodiments overcome more than one issue.

Overview: Event Notification

Some of the embodiments allow applications to subscribe to "events" that correspond to actions in the CAS cloud. The actions that may take place in the CAS cloud include, but are not limited to, the deposition, reading, alteration, or deletion of data. An application (or user) may subscribe for all such actions, or for only those related to a particular group, application, or individual performing the related action. DICOM provides no such event notification. Providing this event notification can simplify the process for an entity to become aware, for example, of new file about which it is interested, regardless of where they are deposited in the CAS cloud. In systems that did not take advantage of event notifications embodiments herein, learning of new files in which the application is interested can be complicated. If a radiology department in Virginia wanted to know if there were new X-rays to analyze from hospitals around the country, then they (e.g., the IT department in Virginia) might set up polling programs that would check specific directories at each hospital (and possibly more than one directory at each hospital). Even in a static national network environment without technical issues, this would be a cumbersome task—and would likely have many technical challenges related to communicating through firewalls, mixed authentication standards, varieties of network and communications capabilities, and ensuring compliance to various standards (e.g., HIPAA or "Health Insurance Portability and Accountability Act"). In a more realistic network environment, all of those problems would exist, and would be exacerbated by the ever-changing network topologies, upgrading of software, storage, and computers, reconfiguration of computers, applications, and the like. In addition, it may be difficult or impossible for the hospital in Virginia to obtain access control information from the various hospitals across the country from which it is polling data. As an example of something that would almost certainly happen without the hospital in Virginia's knowledge: a software administrator at one of the target hospitals changing the directory to which a PACS machine was storing X-rays (possibly to provide more storage). As a result, the polling software in Virginia might either stop working (e.g., if the previous directory disappeared) or not have visibility into updates (e.g., because the new X-rays were being stored elsewhere).

These issues are overcome by some of the embodiments of event notification in a CAS cloud discussed herein. For example, a radiology department's application may subscribe to the deposition of medical images by PACS machines into a particular file directory (perhaps mirrored to the CAS cloud as a bitfile)—or deposited directly into the CAS cloud. Those events may signal that the medical images should be analyzed by the team in Virginia. The team in Virginia receives those notifications without needing to perform the technical connection to the computer or server that deposited the files—and without checking any directories. Further, the hospital in Virginia would receive event notification based on any events in that group (or any group to which subscribes). Further, as discussed with respect to embodiments herein, the CAS cloud can even provide the necessary access control. Related examples are discussed more below with respect to FIG. 4.

Overview: Shared Archive and Related Data

Systems that do not provide a shared archive with searching, and automatic related data searching, are inefficient and may be difficult and time consuming to use. Consider a network of DICOM servers that are all running independent of each other and store their files separately. Since DICOM does not provide a shared archive among DICOM servers, when a doctor wanted to find all of the medical images and reports related to a particular patent, particular examination, etc., the doctor would log into a DICOM server and search for files. Certain files would be returned, but the doctor would have no way of knowing if there were additional files to be found on other DICOM servers, some of which the doctor may not even know about. Additionally, the separate DICOM (or other types of) servers may each have their own identifiers for patients that the doctor may not be aware of. Each server may also have separate access control (e.g., user name and password)—and the doctor may not have log-in or other access information for each server. It would be difficult, extremely time consuming, and in many instances, impossible for the doctor to obtain patient data from all of these servers.

Some embodiments herein provide parsing and archiving of data stored in the CAS cloud, and later search and retrieval of that data, the underlying files, and related data. The data may be stored to, for example, a network-attached storage (NAS) or other computer hard drive by a PACS machine, and simultaneously or subsequently copied to the CAS cloud. PACS machines may write data to drives as single files, often called "blobs." The CAS cloud, regardless of make or model of the PACS machine, will parse the information newly-written to the CAS cloud and add the information for the written data to the archive. For example, consider a PACS machine that writes a blob to its NAS drive that contains two X-rays and an MRI image with corresponding DICOM headers. An application connected to the CAS cloud, upon copying the file from the NAS drive, will parse the DICOM headers and store reference to that file and metadata (from the DICOM headers) in an archive. Embodiments of metadata management for metadata management are given in U.S. patent application Ser. No. 12/605,036, which is hereby incorporated by reference in its entirety for all purposes.

Often image and other medical files have metadata associated therewith, which may be termed "related metadata." The term "metadata" as used herein is a broad term encompassing its plain and ordinary meaning, including but not limited to "data or a set of data that provides information about the data with which it is associated." For example, an X-ray or ultrasound file may have metadata attached thereto (e.g., as a DICOM header or XDS-I header) that describes the X-ray. The metadata may be stored in a structured header, as plain text, etc. Further, some files may contain metadata. For example, an analysis or report may contain metadata as part of the analysis or report (e.g., patient name, data, patient identifier, etc.).

A user with appropriate permissions could search the archive and find (and retrieve) the X-rays and/or the MRI. The user could also search for and retrieve data that had been stored by other PACS machines, ultrasound machines, etc. Additionally, the shared archive can look for related data. For example, if the doctor input a patient identifier for the search, the shared archive may look up that patient identifier in a master patient index to find equivalent entries. The shared archive could then look up related data based on the other patient identifiers from the master patient index. Further, the shared archive may look up related data that is obtained based on data that is retrieved as part of the search. For example, if a query was for 'all data on a patient' (and assuming proper privileges for all data), the first response may be for a particular study. The study will have a unique identifier. The shared archive could then automatically query for all data related to that study number. One of the results of for the study number query may indicate that the patient previously had a different patient identifier. The shared archive could then look up all data for that previous identifier. This process may continue until all appropriate related data is found. In this way, a shared archive with related data search not only collects all of the related data in a way that it may be homogeneously searched, but also provides a way to find related data for queries.

As used herein, the term "patient identifier" is a broad term, encompassing its plain and ordinary meaning, including, but not limited to, "a number, reference, or code that represents a patient in a data system, such as a database, PACS, DICOM message, etc." For example, patient identifiers may include name, social security number, system-specific patient number, Unique Patient Identifier, patient account number, etc. Patient identifiers may also be a combination of one or more of these. For example, a patient identifier may be a combination of patient name and social security number. Patient identifiers may also be unique to a patient across an organization, enterprise, nation, or all system (universal or global).

Overview: Virtual Packages

Grouping data can be difficult in medical systems, yet it is very important. If a doctor would like to group all of the data related to a particular patient, study, series, etc., that doctor would have to find all of the files and burn them to a CD, DVD, or, more likely, numerous CDs or DVDs. In current systems, all of this data may be stored on separate PACS systems, DICOM servers, etc. As noted above and elsewhere herein, merely finding the data that the doctor would like to store package together is difficult or impossible in most systems. Finding the data may require translating patient identifiers from those used in one system to those used in another, mapping accession numbers, manipulating the use of certain data records, etc. Further, these difficulties may be encountered for each server (e.g., a DICOM server or PACS server). For example, a doctor may not even know on which PACS, DICOM, or other server data resides. Even if the doctor knew on which server data resides, the doctor may not be able to find data related to a particular patient, study, series, etc. Further, even if the doctor could find all of this data, she may not be able to store the data to a single CD or DVD. Further, CDs and DVDs can get destroyed, lost, or, worse, fall into the wrong hands. Additionally, the person distributing the package of files may not be able to control the access to the files in the virtual package over time. For example, once a CD or DVD is distributed, even if it has embedded access control, that embedded access control would be static and could not change over time.

Embodiments of virtual packages herein overcome one or more these issues. In creating a virtual package, a doctor may chose to include related data, and, as described elsewhere herein, related data may be automatically discovered and retrieved in a manner that, in many cases, might not be possible for the doctor to do alone. Further, after the virtual package is made and stored in the virtual archive, the doctor can distribute the virtual package without concern for the size of the underlying files. Instead, the virtual package provides a smaller and much more manageable set of data than the underlying files. Additionally, the doctor need not be as concerned with ensuring proper access control. The CAS system provides access control for the files therein, including those in the virtual package. Further, the CAS system can provide access control that varies over time. As discussed in more detail below, access control is being implemented by the CAS system at the time that the files are being accessed. As such, if the access control needs to change over time (e.g., if a malpractice suit was brought, access to data related to that suite may be restricted, monitored, etc.), the CAS can provide that changing access control.

Further Overview

Some embodiments herein cover new approaches for the creation of and access to virtual packages in an interconnected content-addressable storage system. Other embodiments herein provide new and novel techniques for controlling access to data in a content-addressable storage system. Additionally, various embodiments herein provide interfaces for different filesystems heretofore unavailable in the context of content-addressable storage. For example, some of the embodiments herein provide a Common Internet File System ("CIFS") interface. In addition, in some embodiments, data is protected (e.g., by encryption) as it is moved around the cloud, replicated, stored, and/or sent to applications using the cloud.

Details regarding several illustrative preferred embodiments for implementing the system and method described herein are described below with reference to the figures. At times, features of certain embodiments are described below in accordance with that which will be understood or appreciated by a person of ordinary skill in the art to which the system and method described herein pertain. For conciseness and readability, such a "person of ordinary skill in the art" is often referred to as a "skilled artisan."

It will be apparent to a skilled artisan, in light of this disclosure, that the system and method described herein can advantageously be implemented using computer software, hardware, firmware, or any combination of software, hardware, and firmware. In one embodiment, the system is implemented as a number of software modules that comprise computer executable code for performing the functions described herein. In one embodiment, the computer-executable code is executed on one or more general purpose computers. However, a skilled artisan will appreciate, in light of this disclosure, that any module that can be implemented using software to be executed on a general purpose computer can also be implemented using a different combination of hardware, software, or firmware. For example, such a module can be implemented completely in hardware using a combination of integrated circuits. Alternatively or additionally, such a module can be implemented completely or partially using specialized computers designed to perform the particular functions described herein rather than by general purpose computers.

It will also be apparent to a skilled artisan, in light of this disclosure, that the modules described herein can be combined or divided. For example, a skilled artisan will appreciate, in light of this disclosure, that any two or more modules can be combined into one module. Thus, referring to FIG. 1, the CAS server 121 and device manager module 141 may be combined into a single module that performs the functions of both modules. Conversely, any one module can be divided into multiple modules. For example, the CAS server 121 can be divided into multiple modules such that each individual module performs part of the functions of the CAS server 121 and all of the modules collectively perform all such functions.

Similarly, a number of databases are described herein. A skilled artisan will appreciate, in light of this disclosure, that any two or more databases can be combined into one database and that any one database can be divided into multiple databases. A skilled artisan will also appreciate, in light of this disclosure, that multiple distributed computing devices can be substituted for any one computing device illustrated herein. In such distributed embodiments, the functions of the one computing device are distributed such that some functions are performed on each of the distributed computing devices.

The foregoing and other variations understood by a skilled artisan can be made to the embodiments described herein without departing from the spirit of that which is disclosed herein. With the understanding therefore, that the described embodiments are illustrative and that the invention is not limited to the described embodiments, certain embodiments are described below with reference to the drawings.

Exemplary System

"Content-addressed storage," or CAS, as used herein is a broad term, encompassing its plain and ordinary meaning, and includes techniques by which a unit of data stored on a storage system is accessed using an address that is derived from the content of the unit of data. The term "storage identifier" is a broad term, encompassing its plain and ordinary meaning, including, but not limited to a number, reference, pointer, or object that references a memory location, location in a CAS or CAS cloud, or other storage location. One type of storage identifier is a "GUID" or "globally unique identifier." A GUID may be a globally unique identifier that is made sequentially, based on a timestamp, etc. In some embodiments, notwithstanding the potential for collisions, a GUID may be created based on a hash (MD5, SHA, etc.). As an example, the unit of data may be provided as an input to a hashing function which generates a GUID that is used as the content address for the unit of data. When a host computer sends a request to a content-addressable storage server to retrieve a unit of data, the host provides the content address of the unit of data (e.g., a GUID). The storage server then determines, based on the content address, the physical location of the unit of data in the storage server, retrieves the unit of data from that location, and returns the unit of data to the host computer. As used herein, the term "cloud" is a broad term, encompassing its plain and ordinary meaning, including, but not limited to "a shared pool of configurable computing resources (e.g., networks, servers, storage, applications, and services) that can be rapidly provisioned and released with minimal management effort or service provider interaction."

As depicted in FIG. 1, which shows a system 100 for content-addressable storage, a cloud 110 of content-addressable storage servers 121-125, may comprise numerous content-addressable storage servers, and these content-addressable storage servers may be connected in any number of ways. In some embodiments, each content-addressable storage server may be connected to every other content-addressable storage server (not depicted in FIG. 1). In other embodiments, each content-addressable storage server may be connected to one or more of the other content-addressable storage servers in the cloud. Therefore, any communication between two content-addressable storage servers may be over a direct connection, over a single path via one or more of the other content-addressable storage service, or over one or more of multiple paths via one or more of the other content-addressable storage servers. Various direct connections, single path connections, and multipath connections, are depicted in FIG. 1.

The system 100 may include one or more CAS servers 121-125. Each of these CAS servers may include or have thereto attached one or more storage servers (not pictured). The CAS servers may include one or more RAID storage systems, cloud storage, tape storage, optical disks, magnetic disks, and/or any other appropriate type of storage. There may be any number of CAS servers and each may have any number of storage systems. Two or more storage systems may reside on the same physical disk or storage, or each storage system may reside on one or more disks or other storage separate from all of the other storage systems. In some embodiments, content stored in a CAS server 121-125 may be retrieved based on a GUID and/or based on a search, as discussed herein.

As noted herein, when a CAS server 121-125 receives content to store, it may store the content and metadata to the storage system. The content may be stored in the same format in which it is received on an attached memory. In some embodiments, other storage devices or methods may be used, such as flat files, directories, databases, or the like. The metadata may be stored in any fashion, including in a database, flat file, directory of files, or the like. In some embodiments, the metadata may be stored in XML or other structured file as plain text and this plain text may be searchable. In some embodiments, the metadata is stored in a database, and this database may be searchable.

Also depicted in FIG. 1 are three application modules 131-133. The application modules 131-133 can be any type of applications that need storage of data, particularly long-term storage of data that is not going to change quickly. The application modules 131-133, as discussed above, may be medical application modules, and these medical application modules may need access to medical images, such as X-rays, CT scans, MRIs, etc. that have been stored over a period of time. The application modules 131-133 may communicate directly with the cloud 110. In some embodiments, as depicted in FIG. 1, application modules 131-133 may communicate with a device manager module 141-143, respectively. In some embodiments, device manager module 141-143 may provide an interface between an application module 131-133 and the content-addressable storage cloud 110, thereby providing application modules 131-133 with a more traditional data interface than they would have if they were directly coupled to the CAS cloud 110. For example, application modules 131-133 may be able to request or search for data through the device manager module 141-143. Device manager modules 141-143, on the other hand, may act on that request for that search by looking for a global unique identifier, or GUID, that corresponds to the data (perhaps by querying a GUID/Object database 151-153). Once the device manager modules 141-143 have the GUID, they will be able to request the data associated with the GUID either from an attached database (not pictured), or from the content-addressable storage cloud 110.

For example, if a PACS system 131 requests a particular X-ray from device manager module 141, then the device manager module 141 may look up the GUID for that X-ray in its GUID/object database 151. Once the device manager module 141 has the GUID corresponding to the X-ray, it may request the object associated with the GUID from the content-addressable storage server 121. If the content-addressable storage server 121 has the object associated with the GUID, then it will return it to the device manager module 141. If, however, content-addressable storage server 121 does not have the object associated with the GUID stored locally, then it may forward the request for the GUID to one or more other content-addressable storage servers in the cloud 110. Each of the content-addressable storage servers to which the request for the file associated with the GUID was sent will check to see if the object associated with the GUID is stored locally to it. As was the case for content-addressable storage server 121, these content-addressable storage servers to which the request was forwarded will return the object associated with the GUID to content-addressable storage server 121, if it is stored locally. If the content-addressable storage servers to which the request was forwarded do not have the object associated with the GUID stored locally, then they will each forward the request to one or more other content-addressable storage servers in the cloud 110. This process will continue until one of the content-addressable storage servers in the cloud 110 has the object associated with the GUID. Once the object associated with the GUID has been located, it will be returned to content-addressable storage server 121. Content-addressable storage server 121 will then return the object to the device manager module 141, which will in turn provide the object, in this case a file containing an X-ray, to the PACS application module 131.

In various embodiments, after the request for the object associated with the GUID has been satisfied, the object associated with the GUID is cached or stored locally at the content-addressable storage server. Considering the example above, once the content-addressable storage server 121 receives the object associated with the GUID, it may store that object locally (e.g., at CAS server 121). As such any subsequent request for that GUID made to content-addressable storage server 121 may proceed more quickly because the object associated with the GUID is already stored locally at content-addressable storage server 121.

Given that storage is finite, a content-addressable storage server, such as content-addressable storage server 121, may not be able to store objects associated with GUIDs indefinitely. Therefore, various techniques for offloading locally-stored objects to other content-addressable storage servers in the cloud 110 may be used. For example, in some embodiments, after a predetermined amount of time, for example one day, one week, or one month, has passed, an object may be "timed out" and offloaded to another content-addressable storage system in the cloud 110. This timeout technique may be used alone or in conjunction with other techniques. Another technique may be to monitor the quantity or percentage of the storage capacity of the content-addressable storage server 121 that is currently in use. If a certain threshold amount of the storage capacity of the content-addressable storage server 121 is in use, then one or more objects may be offloaded to other content-addressable storage systems in the cloud 110. The choice of which objects to offload may be based on any number of factors, such as the age of the object, the size of the object, or some combination of the two. Many techniques are known to those skilled in the art, including those that may predict which objects are likely to be used in future. In some embodiments, the less likely an object is to be used in the future, the more likely it should be an object chosen to offload onto another content-addressable storage system in the cloud 110.

A user, such as a doctor, may use the shared archive module 133 to query for particular studies (e.g., all X-rays for a particular patient taken in the previous 5 years). The shared archive module 133 may forward the request to the data manager module 143. The data manager module 143 may look up the GUIDs for the X-rays and request that data from the CAS cloud 110. The CAS server 123 may then look locally for the data associated with the GUIDs. If the data associated with the GUIDs are not there, then the request for the GUIDs may be sent into the CAS cloud 110 to obtain the data associated with the GUIDs, as above. Once the CAS server 123 has the data associated with the requested GUIDs, it will send that data to the data manager module 143, which will return it to the requesting application, shared archive module 133. The user will then have local access to the data in the CAS cloud 110.

FIG. 1 depicts a shared archive module 133 that has a shared archive CAS module 143 and a database 153. FIG. 1 depicts the database 153 being connected to the shared archive CAS module 143, but the database 153 may also be directly connected to the shared archive module 133 or connected to both the shared archive CAS module 143 and the shared archive module 133. Further, in some embodiments, two or more of the shared archive module 133, shared archive CAS module 143, and database 153 may be combined as a single unit or module or may run on a single computer (not pictured).

The high-level overview illustrated in FIG. 1 partitions the functionality of the overall system into modules for ease of explanation. It is to be understood, however, that one or more modules may operate as a single unit. Conversely, a single module may comprise one or more subcomponents that are distributed throughout one or more locations. Further, the communication between the modules may occur in a variety of ways, such as hardware implementations (e.g., over a network, serial interface, parallel interface, or internal bus), software implementations (e.g., database, DDE, passing variables), or a combination of hardware and software.

Event Notification

Some embodiments allow users or applications to subscribe to particular event notifications. As noted herein, DICOM does not provide event notification. Nevertheless, users of DICOM and similar protocols and systems may desire or need event notification. Using embodiments herein, users or applications can subscribe to receive event notifications from the CAS cloud. The event notifications may correspond to or be triggered by, events or actions taking place in the CAS cloud. For example, turning to FIG. 1, when a PACS application 131 stores an X-ray, MRI, or other medical image in the content-addressable storage cloud 110, via the data manager module 141, that storage action may be associated with an event. Other applications, such as application 132 may subscribe to events of a particular event type, such as the storage of X-ray images by the PACS application 131. When the PACS application 131 stores the X-ray image to the CAS cloud 110, an associated event notification is propagated through the CAS cloud 110, as represented by the arrows in the CAS cloud 110. For example, the PACS application 131 may store data in the cloud 110 via its local CAS server 121. Its local CAS server 121 may forward a related event notification to the other CASs in the cloud 110, such as CAS server 124. CAS server 124 may in turn forward the event notification to CAS server 125 and, subsequently, CAS server 125 may forward that event notification to CAS server 122. The device manager module 142 or the application 132 may then receive the event notification from CAS server 122. In order to receive the notification, the application 132 may communicate directly with CAS server 122 or to device manager module 142 which may in turn speak to CAS server 122. Various other embodiments of event notification automation are described herein.

As used herein, the term "event notification" is a broad term, encompassing its plain and ordinary meaning, including, but not limited a notification that a particular event has taken place. The types of notifications and their delivery are discussed herein. The term "event" as used herein is a broad term, encompassing its plain and ordinary meaning, including, but not limited to, execution or performance of a particular action with respect to data in a CAS cloud or with respect to the CAS cloud itself. Particular examples of events are described herein.

Figure 2:
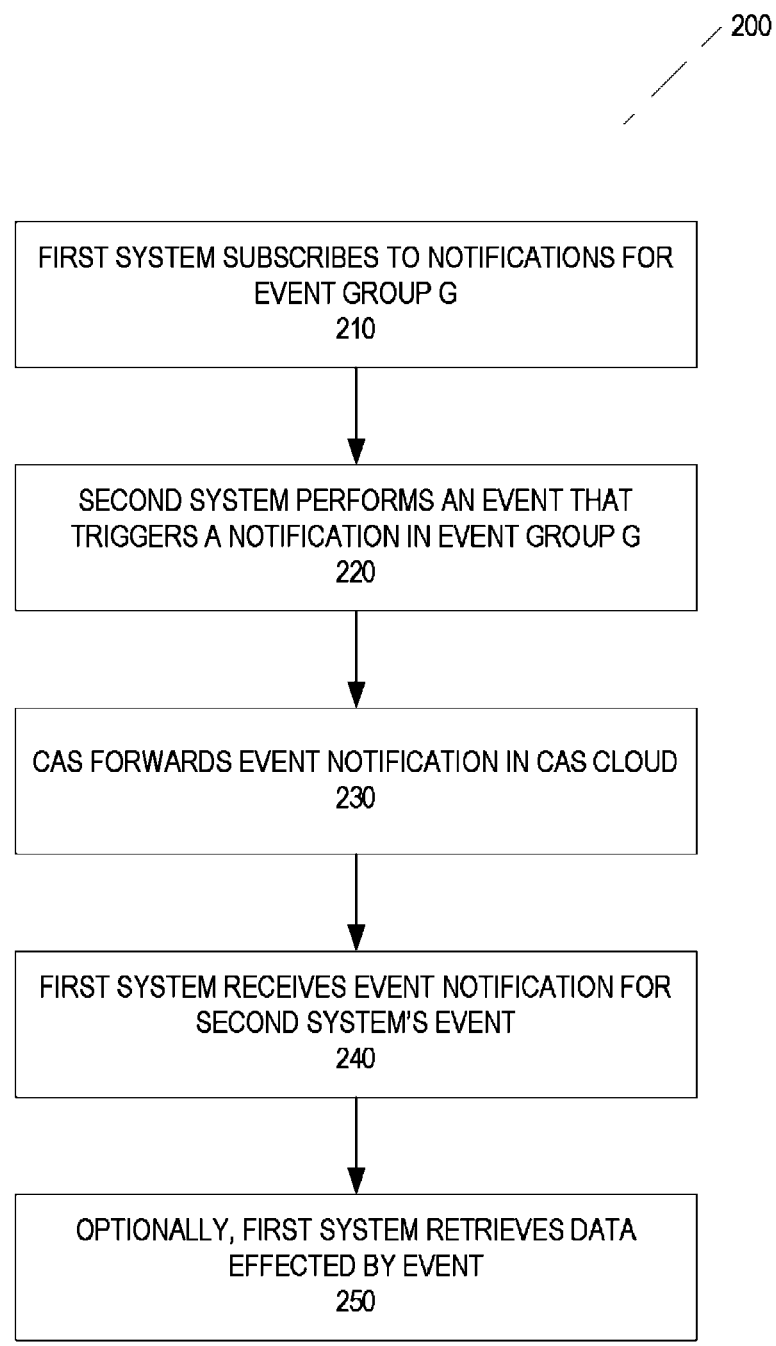
FIG. 2 is a block diagram representing an exemplary process for event notification in a system of interconnected content-addressable storage systems.

FIG. 2 is a flow diagram depicting a method 200 for event notification automation. In block 210, a first system subscribes to an event notification for an event group "G." Returning again to FIG. 1, the first system may be, for example, application 132. The group G may represent any type of group for which application 132 may want to receive event notifications. For example, the group G may correspond to all events for a particular department in a hospital, for a particular hospital, for a particular doctor for all medical images of a certain type, such as X-rays, MRIs, etc.—or any other appropriate grouping. The group G may be defined by any combination of one or more of patient identity, doctor identity, hospital department, hospital, timing, or any other appropriate aspect. The types of events in group G may also be limited to data being written to the CAS cloud 110, data being modified in the CAS cloud 110, and/or data being deleted from the CAS cloud 110. Additional grouping characteristics for event types for a group may also include, for example, storage, retrieval, migration, reloading, deleting, getting properties, changing groups, duplicating bit file, burning a volume, any check or analysis on the CAS cloud, any synchronization or action such as a shutdown initialization, purging in the CAS cloud, etc. In addition, application 132 may subscribe to events associated with all actions in the CAS cloud 110. Turning to specific examples of notifications, in some embodiments, all event notifications have a Group ID (e.g., event group "G" discussed above) and GUID in the body of the notification. An application or server may check all newly-arrived event notifications and find those to which it is subscribed by matching or filtering for the Group IDs in which it is interested.

Method 200 depicts only a single event notification subscription. Nonetheless, systems may subscribe to event notifications for additional actions and/or for different groups other than group G. Various embodiments will allow the first subscriber system to subscribe to event notifications for multiple groups and for multiple event types and perform the subsequent blocks 220-240 and optionally 250 for those other event notifications. For example, application 132 may subscribe to events related to all deletions of X-ray files from a particular hospital, all additions of X-ray files from a particular hospital, and/or all maintenance issues with the CAS cloud.

After the first system subscribes to event notifications for group G in block 210, a second system performs an event that triggers an event notification for group G in block 220. For example, if application 132 subscribed to events for X-rays being written to the CAS cloud at a particular hospital in block 210, and PACS application 131 triggers an event in that group by writing an X-ray to the CAS cloud from that particular hospital in block 220. That event notification would get propagated through the CAS cloud 110 to CAS server 122 as part of block 230.

The forwarding of event notifications in the CAS cloud in block 230 can take many forms in various embodiments. For example, turning to FIG. 1, each CAS server 121-125 may forward the event notifications to every CAS server 121-125 to which it is connected unless it is the CAS server 121-125 from which it received the event notification. In this way, CAS server 121 would forward the event notification to CAS server 124 as well as any other CAS servers to which it is attached. CAS server 124 would then forward the event notification to all CAS servers 123, 125, and any others to which it is connected other than CAS server 121, from which it received the event notification originally. Subsequently, each receiving CAS server will forward it to its other neighbors until all CAS servers in the cloud have received the event notification. In other embodiments, the CAS servers may form a tree or hierarchy which defines to which neighboring CAS servers each CAS server should forward the message, thereby eliminating some or all duplicate event notifications being received at CAS servers in the CAS cloud 110.

In some embodiments, each event notification has associated with it an identifier or signature. That identifier or signature may allow a CAS server 121-125 in cloud 110 to identify if the CAS server 121-125 has received a duplicate event notification. Where appropriate, embodiments ignore duplicate event notifications and provide only the first of duplicate event notifications to subscribers. The CAS servers 121-125 may also forward only the first event notification received and, upon checking the unique identified with subsequent event notifications, not forward any duplicate event notifications to its neighboring CAS servers in the cloud 110. An event notification may include a reference (e.g., a GUID) to the data associated with the action that was performed as well as a group ID, timing, identity, and/or the type of event.

After the event notification is forwarded to the CAS cloud in block 230, the first system will receive the event notification for the event in block 240. The first system may receive the event notification by performing a polling action, such as running a recurrent script or a program that monitors events in the CAS cloud. For example, an application 132 may run a program that continually monitors a location associated with storing new event notifications in CAS server 122. When a new notification arrives, the application 132 or the event monitoring program may compare the incoming notification's group ID with the group IDs for which application 132 has subscriptions. If a matching group ID is found, then the application 132 is then aware of the new event notification. In some embodiments, the CAS server 122 and/or another application in the CAS cloud 110 may have a subscription manager (not depicted in FIG. 1), which will push events to a device manager module 142 or an application 132 in order to provide application 132 with updates on events for which it has subscriptions. In such an embodiment, the subscription manager will check on newly arrived events in the CAS cloud 110 and check the group IDs against the subscriptions of application 132 and/or device manager module 142. If a matching group ID is found, the subscription manager will send the event to application 132 and/or device manager module 142.

After the first system receives event notification for the event related to the action performed by the second system in block 240, the first system may, optionally, retrieve data effected by or associated with the event from the CAS cloud 110. For example, if application 132 has subscribed to a group of events associated with the PACS application 131 writing X-rays to the cloud 110, then upon the PACS application writing an X-ray to the cloud 110, application 132 should receive a notice (blocks 210-240). Application 132 may then retrieve the GUID from the event notification and retrieve the data associated with the event from the CAS using the GUID. Application 132 can then retrieve the X-ray in block 250. A subscription module may also automatically retrieve the data associated with the event and send it to application 132 and/or device manager module 142. As noted above, retrieving data from a CAS cloud 110 may involve querying the device manager module 142 or the application 132 may be able to request the file corresponding to the GUID directly from the CAS cloud 110.

Event notification embodiments herein may be implemented as a parallel to or as part of an implementation of the HL-7 standard. For example, event notification may be implemented to represent Instance Availability Notifications to the systems using IHE/HL-7. The HL-7 Instance Availability Notification may be implemented, for instance, using the event notification in the CAS as described herein. The storage of a file in the CAS cloud may trigger an event notification, sent as an Instance Availability Notification. The event notification may notify interested workflow actors (such as an IHE Department System Scheduler/Order Filler, Post-Processing Manager and Report Manager, etc.) about the availability status of data in the CAS. The messages may be sent using an HL-7 Observation Results Unsolicited message, Medical Document Management message, or any other appropriate message type.

Example Workflow Using Event Notification

Figure 3:
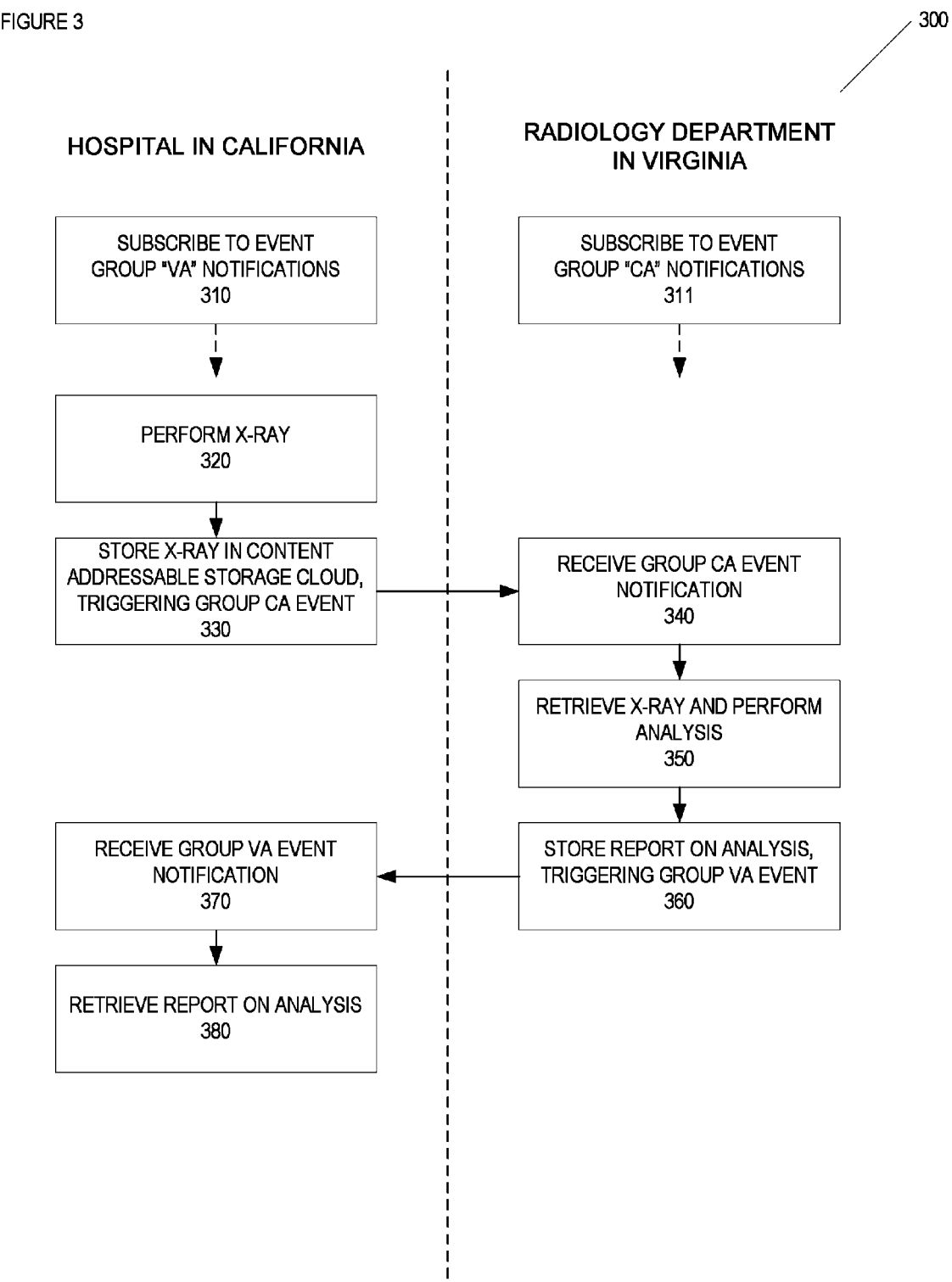
FIG. 3 is a block diagram representing a second exemplary process for event notification in a system of interconnected content-addressable storage systems.

FIG. 3 illustrates an abstract representation of an example workflow for two medical service providers connected to a content-addressable storage server cloud. The first hospital is in California and the second is associated with a radiology department in Virginia, both of which may be connected to the same CAS cloud 110 in FIG. 1. The hospital in California subscribes to receive event Group "VA" event notifications in block 310. The Group VA event notifications may be, for example, when the group in Virginia has stored reports on analysis of medical imagery in the content-addressable storage cloud. The radiology department in Virginia, on the other hand, may subscribe to receive event Group "CA" event notifications in block 311. The Group CA may correspond to X-rays being deposited or stored in the CAS cloud. After the two medical service providers have subscribed to events, they may later receive event notifications, as represented by the two dashed arrows in FIG. 3. In the example below, the California hospital performs an X-ray, the Radiology Department in Virginia analyzes the X-ray, and the California hospital receives a notification of that analysis. Many other workflows are also possible with embodiments herein. Different imagery may be used (MRI, ultrasound, etc.) or no imagery may be used at all. For example, the events and workflows may be related to analysis of written reports, proofreading, transcription, or any other appropriate workflow or analysis.

In block 320, an X-ray is performed at the hospital in California. The X-ray may be performed using any known means, technique, or method. In block 330, the X-ray is stored in the content-addressable storage server cloud thereby triggering a Group CA event notification. Storing the X-ray to a CAS server or cloud may include writing it to a CAS server or cloud directly using a CAS interface, writing to a directory that is mirrored to a CAS server or cloud, writing to a file system interface that interfaces with the CAS server or cloud, or any other appropriate method, system, or technique. For example, referring to FIG. 1, a PACS application 131 or a device manager module 141 may write the X-ray to a NAS or other directory, which may then mirror the X-ray to the CAS server or cloud (possibly with header or other files or information as part of the same file). "Mirroring" a folder or directory to the CAS cloud 110 may take many forms, including replicating the folder as a single bit file in the CAS cloud 110 or individual files in the directory may be stored in the CAS cloud 110 and the structure of the folder (e.g., mapping of GUIDs for particular files to corresponding directories) may be stored separately (e.g., also in the CAS cloud 110 or at PACS application 131 or device manager module 141).

Triggering the Group CA event may include content-addressable storage systems that are interconnected in a CAS cloud 110 forwarding the events until each content-addressable storage system in the CAS cloud 110 has received the event notification or at the very least until a CAS server connected to the radiology department in Virginia receives the event notification. Numerous examples of generating or triggering event notifications are described in detail elsewhere herein.

In block 340, the radiology department in Virginia receives the Group CA event notification. Receiving that notification may spawn under number of workflows including emailing a radiologist, populating a database or to-do list at a radiologist's workstation, inserting an X-ray into a radiology workflow or queue, etc. In this way a radiologist may be able notified that a new X-ray, is available and needs analysis.

In some embodiments, block 350 may include manually or automatically retrieving the X-ray from the CAS server or cloud after the event notification is received. Block 350 may also include the radiologist performing analysis of the X-ray. After analyzing the received X-ray, the radiologist may store a report on that analysis into the content-addressable storage system or cloud, thereby triggering a Group VA event notification in block 360. The report may include the radiologist's opinion, analysis, annotations, or any other information or work product that has been made by the radiologist. As described elsewhere herein, storing to a CAS server or cloud may include writing the report to a directory and that directory being copied to the content-addressable storage server; writing to a network attached storage system, where that network attached storage system operating as an interface for the content-addressable storage system; storing the report directly to a CAS server via a CAS interface or to the cloud; or any other appropriate writing means or technique. Referring to FIG. 1, either an application 132 or a device manager module 142 may control the writing of the report to the CAS server 122 or CAS cloud 110.

The Group VA event notification generated by the radiologist's report being stored on the content-addressable storage server or cloud (block 360) is propagated through the content-addressable storage server cloud and received at the hospital in California in block 370. Receiving the Group VA event notification in block 370 may spawn another workflow or actions, such as sending an email to an appropriate doctor, team of doctors, administrators, or other practitioners, etc.

Receiving the Group VA event notification in block 370 may be followed by storing an indication of the event in a database, file, or queue. Any other appropriate notifications or actions may be taken based on the receipt of the Group VA event notification.

Once the event notification is received in block 370, the report or analysis may be retrieved in block 380. The report may be retrieved in any appropriate manner, including those techniques discussed herein. For example, a doctor may retrieve the report from the CAS cloud 110 based on the GUID in the Group VA event notification using an application 131-133. The application may, in turn, use the data manager module 141-143 to retrieve the report stored from the CAS cloud 110. Regardless of which way the report or analysis is retrieved, the doctor may then review the analysis and continue patient care. From there the doctor may be able to review that analysis and discuss it with a patient as appropriate. For example, using the techniques of FIG. 3, the doctor who originally performed the X-ray in California may later receive an email that the radiology department in Virginia analyzed the X-ray and can now retrieve and review the report with the patient.

Numerous other workflows or methods may be performed using various embodiments herein. Those embodiments may incorporate complex workflows and notifications associated with each block in the workflow in order to trigger further action, such as depicted in method 300 of FIG. 3. For example, a technician may perform an ultrasound and store the ultrasound data in the content-addressable storage server cloud. Storage of that ultrasound data may generate an event for a radiology department to analyze it. The analysis may then be performed, and a report on the analysis stored in the content-addressable storage server cloud, thereby generating its own event notification. A doctor may then be notified of that the report on the ultrasound is ready for review. The doctor may retrieve the ultrasound data and related report from the content-addressable storage server cloud and perform further review on the ultrasound and the report. The doctor may then discuss the report or findings with the patient and possibly perform another ultrasound. This further ultrasound may again be deposited in the CAS, which will again trigger the radiology department to perform analysis. And the workflow may be extended and/or repeated.

Shared Archive

Embodiments herein provide a shared archive in an interconnected content-addressable storage system. For example, looking at FIG. 1, an application 132 and a PACS application 131 may each store information in a content-addressable storage server cloud 110. Upon storage of information in the content-addressable storage server cloud 110, an application, such as shared archive module 133 or shared archive CAS module 143, may parse the incoming files being stored in the content-addressable storage server cloud 110. Upon parsing these incoming files, the shared archive may extract information from the metadata in those files and store the information (perhaps database 153). As used herein and in this context, the term "information" is a broad term, encompassing its plain and ordinary meaning, including, but not limited to "data or metadata in a parsed or otherwise accessible form." For example, when metadata is parsed, the information from the metadata may be accessible, for example, in RAM in a data structure, as entries in a database, etc.

At a later time, a user (not pictured in FIG. 1) may access the shared archive module 133 and query for files stored in the CAS cloud 110. The query may be for a particular type of image, such as an MRI image, a particular patient, a particular doctor, or a particular hospital. Upon receiving the query, the shared archive may search the database 153 for records that match the query and related data. The shared archive module 133 may then return results to the requester (e.g., the one that sent the query) in the form of GUIDs for the files that correspond to the metadata. The response to the query may be the metadata itself, a report on the metadata, or any other appropriate information related to the metadata. In some embodiments, the shared archive may return all or a part of the file(s) matching the query.

Figure 4:
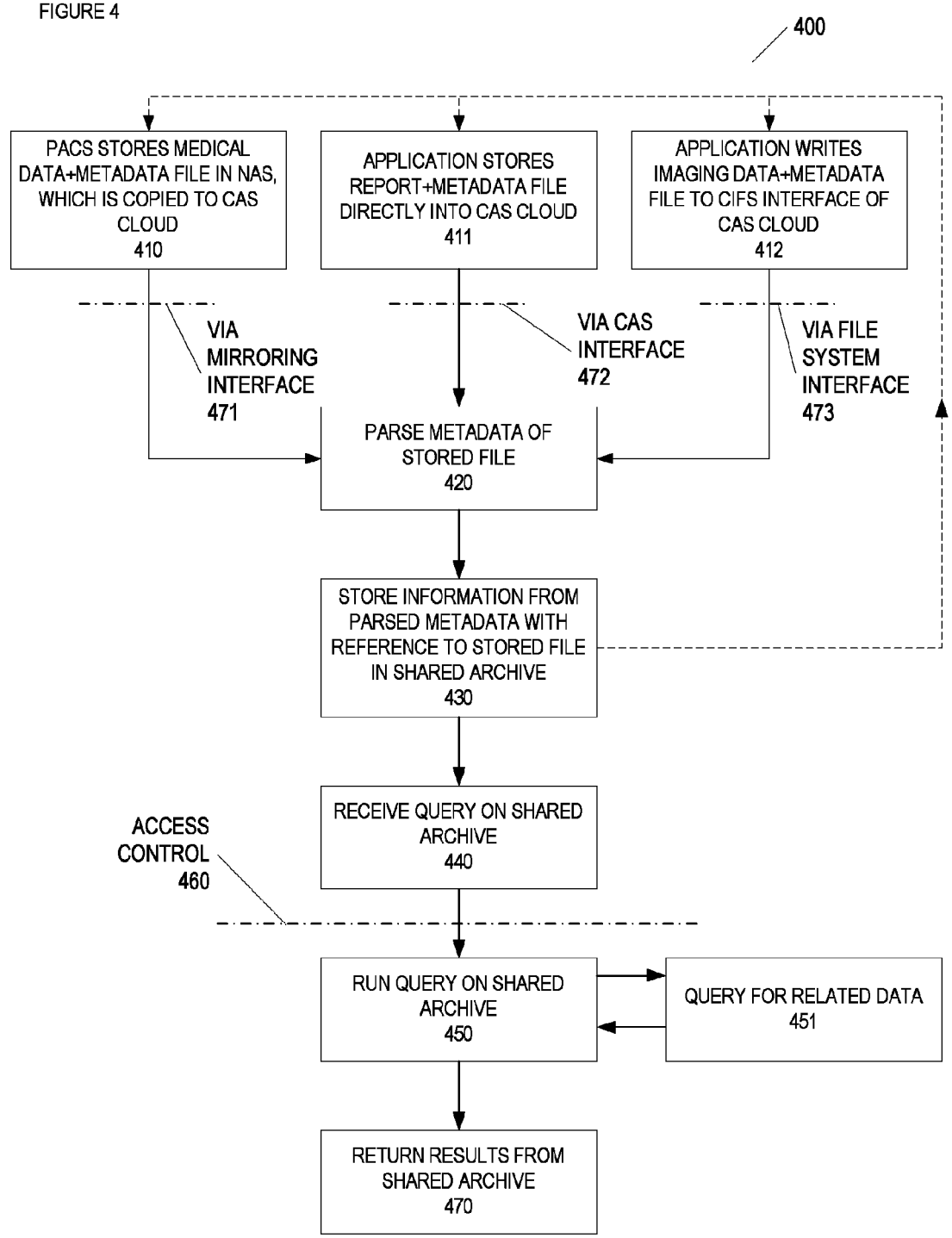
FIG. 4 is a block diagram representing an exemplary process for providing a shared archive in a system of interconnected content-addressable storage systems.

Turning now to FIG. 4, a flow diagram depicts a method 400 for providing a shared archive. In block 410, a PACS machine stores a file containing medical data (such as imaging data) and related metadata to a disk drive, such as a network-attached storage drive. In this particular embodiment, the network-attached storage drive is mirrored to the CAS cloud as part of block 410. This is represented with the mirroring interface 471 depicted in FIG. 4. Mirroring a directory or drive may include copying all files from one or more directories onto other drives (or into other directories). Redundant Array of Independent Disks (RAID) is one example of using mirroring techniques. If a local or networked drive (or directory) is mirrored to the CAS, then as files are copied to that drive (or directory) are copied to the CAS. For example, turning to FIG. 1, if a PACS application 131 stores a file to a mirrored directory, the data manager module 141 may then copy that file from the mirrored directory to CAS server 121, which will return a GUID for the file. The GUID may be stored in the GUID/OBJ database 151 along with information about the stored file. As used herein, the term "medical data" is a broad term, encompassing its plain and ordinary meaning, including but not limited to images, videos, reports, and other medical-related data associated with one or more patients, accession numbers, study numbers, series numbers, etc. Medical data may include or have associated with it related metadata. Examples of medical data include, but are not limited to DICOM images, DICOM reports, files in a proprietary format that have header data or metadata, XDS-I-encapsulated files or reports, or any other appropriate data image or metadata.

Various embodiments provide for other sources of files for inclusion in the shared archive. For example, block 411 depicts an application storing a file, which contains a report and metadata, directly into the CAS cloud via a CAS interface 472. The CAS interface 472 is described extensively above with respect to FIG. 1 and elsewhere herein. Another source of data is depicted in block 412. In block 412, an application writes a file containing imaging data and metadata to a CAS cloud via a file system (e.g., CIFS) interface 473. A CIFS interface may be particularly useful for legacy applications that communicate directly to a CIFS drive. That is, the application may be able to believe that it is writing to a network-based CIFS drive and, in fact, the application is instead writing to the CAS cloud. Implementations of network interfaces, such as CIFS interfaces, are described elsewhere herein and various embodiments herein include other files system interfaces, such as NFS, FAT, SAMBA, etc. There may be additional ways to store files and data into the content-addressable storage cloud and these are considered within the scope of embodiments herein.

After a file is stored in the CAS, then, in block 420, the metadata of the stored file is parsed. In some embodiments, the stored files may have a single header containing metadata related to a report, image, or other documents stored therein. For example, an XDS-I file has a header and an encapsulated file portion and the XDS-I header may have parsable metadata which is parsed and used in the subsequent blocks of method 400. As another example, a DICOM header may include a preamble and a prefix followed by numerous data elements. The header may contain data describing the data elements stored in the file. This header information is parsed in order to extract information about the subsequent data elements in the DICOM file. Some files stored in the CAS cloud are files known as "blobs." Blobs may contain multiple DICOM files and/or other format files. For example, if a blob contains multiple DICOM files, then each header may be separately parsed and information extracted about the data elements following each header. A similar process occurs regardless of the type of file stored in the CAS cloud.

Headers can be parsed based on the format of the file and header. Some headers are in a mark-up language format and can be parsed based on that mark-up language. For example, XDS-I headers are typically in XML or a related mark-up language. Other headers, such as DICOM headers, may have fields that identify and define where and what type of information is in the header. Other formats and methods of parsing them are also encompassed by the embodiments herein.

Once the metadata of the stored file is parsed in block 420, the information extracted from the parsed metadata is stored in the shared archive with a reference (e.g., a GUID) to the file itself. For example, if a DICOM image containing an X-ray is parsed in block 420 and patient name, doctor, time of performance of the X-ray, and hospital is extracted from the DICOM header in block 420, then in block 430 this information is stored in the shared archive and associated with the GUID of the stored DICOM file.

When information is stored in the shared archive in block 430 of FIG. 4, the shared archive module 133 may take the information obtained from parsing the file stored in the CAS and store it in database 153 along with the GUID or other identifier that is associated with the metadata. In this way, a user may later be able to search the information in the database 153 to find matching files and retrieve the GUIDs and/or the files.

Returning again to FIG. 4, there is a dotted line from block 430 back to blocks 410, 411 and 412. This dotted line represents that the actions related to blocks 410-430 may repeat. Furthermore, the actions related to blocks 410-430 may repeat multiple times asynchronously with the actions in blocks 440 and 450. For example, multiple files may be stored in the CAS cloud sequentially or at the same time (blocks 410-412) and the metadata for each of those files may be parsed (block 420) and stored in the shared archive (block 430). This process can continue notwithstanding that queries may be received on the shared archive. That is, when a query is received on the shared archive (block 440), the query will be run on whichever data has already been parsed from files stored in the CAS (e.g., the latest information available).

In block 440, a query is received on the shared archive. The query may be of any appropriate type (Boolean, SQL, natural language, DICOM Query/Retrieve, etc.). The query may be for X-rays for a particular patient, all images for a particular patient, all files (e.g., reports, images, etc.) for a particular patient, all files or a subset of files for a particular doctor, all files or a subset of files for a particular department in a hospital or a particular hospital, etc. Additionally, the queries may be for particular periods of time, for example, all X-rays stored with relation to a particular patient between Jan. 1, 2009 and Jan. 12, 2009.

Once the query is received in block 440, the query is run on the shared archive in block 450. Running the query may simply comprise running a query on database 153. There may also be interpretation of the received query in order to run the query on database 153. For example, the query may request results related to a particular patient. Those results may then be the basis of more queries for related data in block 451. From the first results received, one or more queryable data items may be extracted. As used herein, the term "queryable data item" is a broad term encompassing its plain and ordinary meaning, including, but not limited to, a data item for which a search may be performed. In this context, the queryable data item may be one or more data items, obtained from the search results, for which subsequent queries or searches may be run. For example, a query for an X-ray could return an X-ray that is associated with a particular accession number. The shared archive, in block 451, may then perform another query, on the accession number, to find related data. An "accession number" as used herein is a broad term that encompasses its plain and ordinary meaning, including, but not limited to, a number or identifier that identifies a particular object or collection of objects (such as a particular lab results or set of lab results).

Requesting related data can be a very complex undertaking. In an interconnected system in which all of the interconnected systems and servers are using a shared identifier, requesting related data may simply include sending requests to those connected servers and systems for all data related to that identifier. In many modern hospitals and healthcare systems, however, different identifiers are used by different systems within the same interconnected medical environment. For example, one imaging server may identify patients by social security number. Another may identify patients by a patient identifier generated by that system or some other centralized system. In addition, even if the multiple systems start with the same identifier, they may prepend or append information such as time stamps or locations onto the identifier in order to identify that patient study or accession uniquely.

Figure 8:
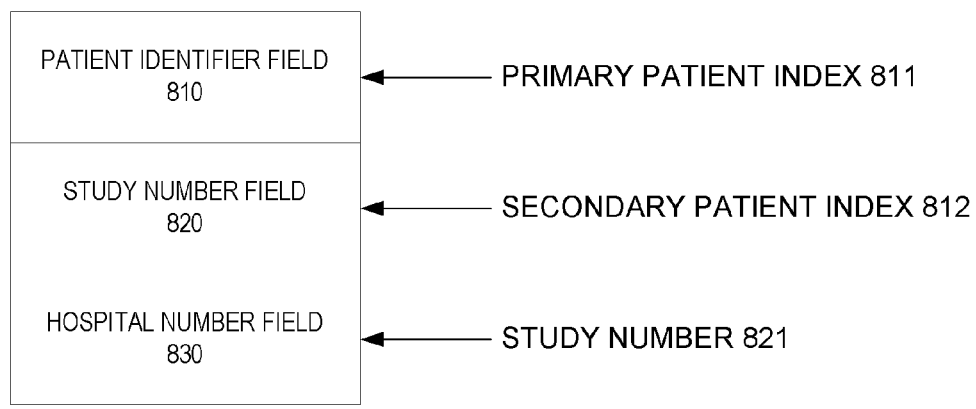
FIG. 8 is a block diagram representing an exemplary data structure and data in a system of interconnected content-addressable storage systems.

In addition to the difficulty related to the use of different identifiers, systems may codify or place identifiers in different or inconsistent locations. For example, consider a PACS system or other imaging system in which there is only a single field for the patient identifier. Some hospital systems may also use hierarchies of patient identifiers in order to identify the patient correctly across a broad range of systems. An imaging system that only has a single location to store a patient identifier with a record may then have to be modified or treated differently. For example, one of the two patient identifiers needed may be stored in the space provided on that system for the single patient identifier. The other patient identifier on the other hand, may be stored in another field, such as an accession field, middle name field, or comment field. Further, because that other field is used for a secondary purpose, the information that would have originally gone into that field may have to be placed in another location. This process may continue and numerous fields may be used inconsistently or in a nonstandard way in the system. For example, turning to FIG. 8, there is a data structure 800 that contains a patient identifier field 810, a study number field 820, and a hospital number field 830. As indicated by the three dots, there may be numerous other fields. If a system needs to store two patient indices, then data structure 800 may not provide sufficient fields. The primary patient index 811 may have to be stored in the patient identifier field 810. The secondary patient index 812 may be stored in the study number field 820, and the study number 821 may be stored in the hospital number field 830. Other changes may have to be propagated through the rest of data structure 800. As a result of inconsistent use of the field in the data structure, requesting related data from a system may require knowing how the data structures or other pertinent identifiers are used within that system. A system wishing to talk to a PACS that uses the data structure 800 in FIG. 8 would have to know to send its primary patient index in the data structures field 810, its secondary patient index in the study number field 820, the study number in the hospital number field 830, etc. Additional embodiments of searching for related data are discussed elsewhere herein.

As another example, a query for all data on a patient identifier (block 450) may result in results associated with numerous accession numbers, study numbers, serried numbers, etc. In block 451, queries may be run on the returned accession numbers, study numbers, series numbers, etc. Those queries may, in turn, results in other identifiers being discovered (related to other accession numbers, series numbers, study numbers, and possibly other patient or data indices). Each of those new identifiers may also be searched and return results. In addition, the query may be translated using a master patient index to run the query on other identities associated with the patient (e.g., other patient identifiers, social security numbers, etc.). Master patient indexes are described elsewhere herein. As an example, however, a patient may be assigned an index upon a first visit to the hospital, and, years later, be assigned another. This relationship may be stored in the master patient index. As another example, people may change their names over time. The relationship between these two names may be stored in the master patient index. For each of the queries for the identities found in the master patient index, additional related data queries may also be run (block 451).

Blocks 450 and 451 may incorporate access control for queries. The access control may be such that only particular users are allowed access to particular types of data. As such, data and related data may not be retrieved in blocks 450 and 451 unless there is proper access rights, or data may not retrieved and not sent to the requestor unless there are access rights (e.g., in block 470). Additionally, there may be classes or sets of users, for example, doctors may be allowed access to certain types of data, patients only to data about themselves, and administrators may have access to all data. For example, block 440 may include access control (460) and may not perform a query if the requester does not have proper access to data or information that would be returned. Further (not depicted in FIG. 4), a user may not even be able to log into or present a query to a shared archive (which in some embodiments requires users to log in) if that user does not have proper access. HIPAA provides requirements on data access control and data encryption for some entities. In embodiments herein, these requirements are implemented as part of block 450, 451, 460, or as part of other blocks in FIG. 4. Turning to FIG. 1, the shared archive module 133 and/or the shared archive CAS module 143 may provide access control. The access control may be such that it corresponds to HIPAA's requirements for data security and integrity or any other appropriate access control in which only certain users or classes of users have access to certain types of data.

Once the query is run and results are received, block 470 may include returning those results to the requester (e.g., the person or system that sent the query). Returning the results to the requester may include returning GUIDs to the data files stored in the CAS cloud that match the query. The results may also be returned as a report or list of metadata or the files associated with the matching metadata may be returned. For example, if a requester requests X-ray files from Jan. 1, 2009 to Jan. 12, 2009 for a particular patient, and three X-rays are found, then the shared archive module may return GUIDs associated with those three X-rays or may return files containing the three X-rays, such as DICOM files (e.g., via a DICOM Store command).

As another example, an application may perform a DICOM Query/Retrieve using embodiments of the shared archive. For example, the application may perform a DICOM Query to the shared archive requesting data for a patient name, patient ID, accession number, physician, etc. The shared archive may receive the DICOM Query (block 440) and perform a search for the patient name, patient ID, accession number, physician, etc. (block 450). The shared archive may also query for related data (block 451). The shared archive may then return the results of the query (block 470). The requesting application may then perform a DICOM Retrieve for the studies or other data that were returned as part of the DICOM Query. This DICOM Retrieve may be performed as part of block 440 or may be executed by a block not shown in FIG. 4. The shared archive may then retrieve the data requested in the DICOM Retrieve and may return the data to the requester as part of a DICOM Storage command. In some embodiments, the DICOM Retrieve may be sent to a server other than the shared archive. For example, the DICOM Retrieve could be sent to a CAS server and the CAS server could look up the GUID for the requested file and retrieve and send the file (e.g., via a DICOM Storage message) to the requesting application.

The discussion with respect to FIG. 4 and method 400 is primarily focused on files that contain medical data (e.g., reports or imaging data) and metadata. Any other appropriate file may also be used. For example, a report stored in the CAS cloud may contain metadata and not have a separate header. That report may be parsed and may be made searchable in a shared archive using method 400. In addition, files containing test results may also be storable, parsable, and later searchable. In this way, the shared archive module may provide homogeneous access to data that has been stored in a heterogeneous manner in the CAS cloud 110. Such homogeneous access is particularly beneficial considering that embodiments of the CAS cloud allow legacy systems to store to the CAS cloud (e.g., though mirroring or network interfaces to the CAS) in addition to newly developed systems to store to the CAS cloud. In this way, various applications as well as multiple types of data can be stored in the CAS cloud and accessed jointly and efficiently in a shared manner from the shared archive module.

Shared Archives and Document Sharing Protocols

Document sharing can be an important part of management and communication of information. In addition to the shared archive embodiments described herein, various embodiments provide a document sharing protocols (such as XDS and XDS-I) and, in some cases, integrated shared archives. There are many efforts to standardize the management and sharing of documents. One such project is the organization Integrating the Healthcare Enterprise's (IRE) effort known as cross-enterprise Document Sharing (XDS). IRE has created a follow-on standardization effort known as the cross-enterprise Document Sharing for Imaging (XDS-I). XDS-I extends XDS by enabling the sharing, locating, and accessing of DICOM images and other documents that may be received from or accessed by, e.g., radiology centers, hospitals, doctors offices, or any other applicable source or consumer. XDS-I may be useful for sharing X-rays, MRIs, and other health records, such as cardiology documents. XDS and XDS-I implementations may be built on the principle that one is able to query a single source in order to obtain access to stored documents from any of multiple repositories. As such, various embodiments herein may provide an XDS-I storage, searching, and retrieval interface that provides access to underlying documents stored in a CAS or CAS cloud.

Figure 5:
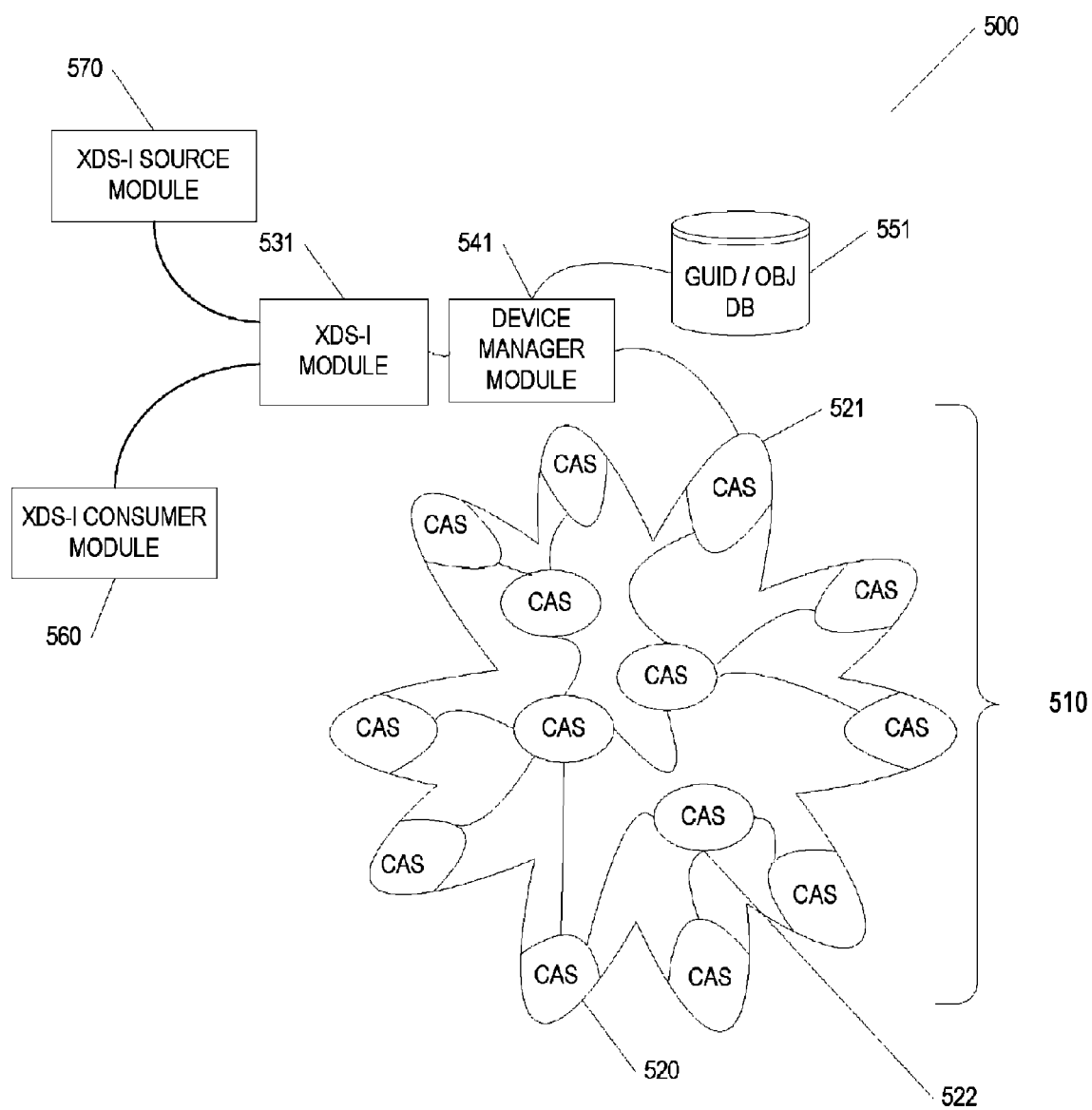
FIG. 5 illustrates a second block diagram of an exemplary embodiment of a system for content sharing with interconnected content-addressable storage systems.

As depicted in FIG. 5, various embodiments herein provide document sharing by providing modules, such as XDS-I module 531. In some embodiments, XDS-I module 531 can address cross-enterprise EHR communication needs. Some scenarios may require the use of other IRE integration profiles, such as Patient Identifier Cross-Referencing (PIX), Audit Trail and Node Authentication (ATNA), Enterprise User Authentication (EUA), Cross-enterprise User Authentication (XUA) and Retrieve Information for Display (RID), not depicted in FIG. 5.

As depicted in FIG. 5, cloud 510 includes multiple content-addressable storage servers 520-522. A device manager module 541 may be in communication with cloud 510. Device manager module 541 may have associated with it a GUID/object database 551 and may be coupled to an XDS-I module 531. Various embodiments of communication among clouds, device manager modules, GUID/object databases, and applications are described with respect to FIG. 1. XDS-I module 531 may communicate with various XDS-I actors, such as an XDS-I source module 570 and an XDS-I consumer module 560. The XDS-I module 531 may also communicate with other XDS-I actors and/or other XDS-I modules, not pictured. In some embodiments, the XDS-I source module 570 may be coupled to an image source, such as a CT scanner or X-ray machine. In some embodiments, the XDS-I consumer module 560 may be coupled to a doctor's workstation or a PACS station, not pictured. Various embodiments of system 500 may allow a doctor to access the previously stored medical image, or any other document, regardless of its source, using XDS-I.

Generally, in some embodiments, an XDS-I source module 570 may receive images from an imaging source, such as an MRI, X-ray, CT scan, or other imaging device. The XDS-I source module 570 may then store the received image in the cloud 510 by sending the image, using the XDS-I protocol, to the XDS-I module 531 (e.g., as a DICOM image encapsulated in an XDS-I message). The XDS-I module 531 may then send the image to the device manager module 541 which will then store it to the cloud 510 via the content-addressable storage server module 521, which will in turn return a GUID that corresponds to the stored image to the device manager module 541. The device manager module 541 can store the relationship between the stored image, its metadata, and the corresponding GUID in the GUID/object database 551. In some embodiments, XDS-I module 531 may store metadata related to the stored image in addition to or instead of device manager module 541. Subsequently, when an XDS-I consumer module 560 sends a request to the XDS-I module 531 for that object, the XDS-I module 531 can request that object from the device manager module 541, which will then retrieve it from cloud 510, and send it to the requestor, possibly with additional related data. The described storage, searching, and retrieval of documents may apply, as noted above, to documents other than images, such as electronic health records and the like.

When the XDS-I source module 570 receives an image that it wants to store, e.g., to cloud 510, it may encapsulate the image and add a header containing metadata about the image. The XDS-I source module 570 may also request any of a number of other transactions from the XDS-I module 531. The transaction may include storing a document, altering a stored document, replacing a stored document, etc. Other example transactions and embodiments of transactions are described in the appendices attached to parent U.S. Provisional Application No. 61/327,556, which are hereby incorporated by reference for all purposes.

In some embodiments, when an XDS-I consumer module 560 searches for a document or image, more than one document may match the request. For example, if an XDS-I consumer module 560 requests documents related to a certain patient, then the XDS-I module 531 may determine that multiple patient records and images are related to that patient. The XDS-I module 531 may then present to the XDS-I consumer module 560 a list of all of the matching documents. The XDS-I consumer module 560 may provide the list of matching documents to a user, not pictured, that will allow the user to select one or more of the matching documents for retrieval. The XDS-I consumer module 560 may then request retrieval of all of the selected documents from device manager module 541, which may then look up the GUIDs for those objects in its database 551 and request those objects from the cloud 510. The XDS-I consumer module 560 may also perform other actions, such as (i) retrieve presentation states, which requests and retrieves the Grayscale Softcopy Presentation State (GSPS) information for a particular image or image set; (ii) retrieve reports, which may retrieve a diagnostic report, for example; (iii) retrieve key image notes; and (iv) retrieve evidence documents. More embodiments and examples of various requests are described in the appendices attached to parent U.S. Provisional Application No. 61/327,556, which are hereby incorporated by reference for all purposes.

In some embodiments, the XDS-I module 531 may include or be attached to a metadata database or server, such as shared archive module 133, shared archive CAS module 143, or database 153. The XDS-I module 531 may store therein metadata related to documents that it receives from XDS-I sources and relate them to the GUID that it receives from the device manager module 541 when the XDS-I module 531 stores documents to the cloud 510. For example, when XDS-I module 531 receives an XDS-I message to store an X-ray from XDS-I source module 570, it may store metadata related to the X-ray (e.g., received as part of a header from the XDS-I source module 570) in the metadata database along with the GUID corresponding to the stored X-ray image, received from device manager module 541. In other embodiments, device manager module 541 may store the metadata related to stored images in addition to or instead of XDS-I module 531 storing that data. Further, the device manager module 541 may associate the metadata for those images with the GUIDs for the image in the database 551. In other embodiments, XDS-I module 531 may serve as a shared archive module and perform related functions, such as those described herein.

In some embodiments, when the XDS-I consumer module 560 requests a document, the XDS-I module 531 may retrieve the requested document and other related documents and send them to XDS-I consumer module 560 in a single response message. For example, if the XDS-I consumer module 560 requests an X-ray for a patient, then the XDS-I module 531 may retrieve that X-ray as well as related medical data and return the X-ray and the related medical data as a single XDS-I response. This may take the form of storing related medical data, such as lab results, patient name, etc., in an XDS-I header and the image in the XDS-I message.

In various embodiments, each module in system 500 may run on a separate processor or as part of a separate process. Two or more of the modules may be implemented together or may be run as part of the same process, on the same processor, on the same machine, as part of the same application, and the like. For example, XDS-I module 531 and device manager module 541 may run as part of separate processes or applications, or may be part of the same application or process. As another example, in some embodiments, XDS-I module 531 may also include as part of the same process, or application, either or both of XDS-I source module 570 and XDS-I consumer module 560.

Figure 6:
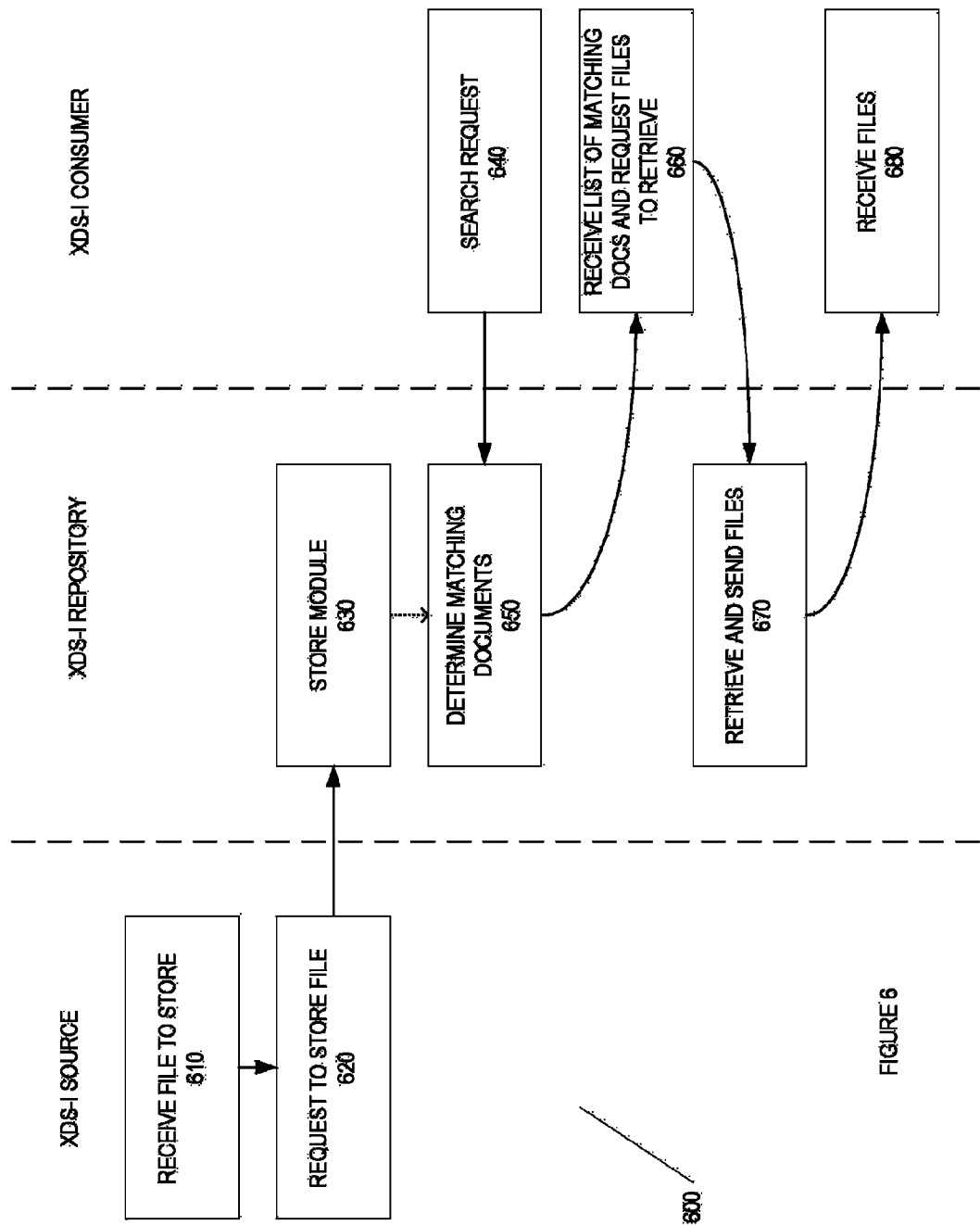
FIG. 6 is a block diagram representing an exemplary process for content sharing in a system of interconnected content-addressable storage systems.

FIG. 6 depicts a method 600 of providing XDS-I support. An XDS-I source may receive a file to store from a user or machine, such as receiving an X-ray from an X-ray machine in block 610. For example, an XDS-I source module 570 may receive an X-ray image to store. In block 620, the XDS-I source requests storage of the file in the XDS-I repository. For example, the XDS-I source module 570 may encapsulate the X-ray image data file in an XDS-I message and send the message to XDS-I module 531 for storage (possibly using encryption for transmission and/or storage). In block 630, an XDS-I repository may receive a request to store a document. For example, XDS-I module 531 may receive the request to store the X-ray image data file encapsulated in the XDS-I message from XDS-I source module 570. In some embodiments, an acknowledgment of storage may be sent back to the XDS-I source, not pictured.

When an XDS-I consumer later requests documents, in block 640, that request is sent to an XDS-I repository and matching documents, possibly including related data and related documents, are determined as part of block 650. The XDS-I repository may then send a list of matching documents to the XDS-I consumer, which will receive them in block 660. For example, XDS-I consumer module 560 may send the request for documents related to a particular patient to XDS-I module 531. XDS-I module 531 may then search for relevant documents and send the list of those documents to the XDS-I consumer module 560. Returning again to FIG. 5, the XDS-I consumer, in block 660, may request certain files that were found. In block 670, an XDS-I repository may send the requested files to the XDS-I consumer, who may receive them in block 680. For example, XDS-I consumer module 560 may request certain files of those that were previously found in block 650 from the XDS-I module 531. The XDS-I module 531 may retrieve those files from the cloud 510 via the device manager module 541 and send those files to the XDS-I consumer module 560.

In some embodiments, a search requested in block 640 may include a request to immediately retrieve all documents matching the search, and block 650 may include retrieving those documents and sending them to the consumer who will receive them in block 660.

In some embodiments, system 500 and method 600 may also include a security model that may be associated with an XDS-I Clinical Affinity Domain. For example, embodiments may group XDS-I Actors with actors from the IRE Audit Trail and Node Authentication (described elsewhere) and may include access control capabilities that operate in cross-enterprise environments. Example embodiments include Public Key Infrastructure, and those related to ATNA, etc. In some embodiments, XDS-I modules may also be joined together or federated and thereby provide access to patient records as patients move from region to region, or country to country.

In addition to being able to provide functionality and support related to XDS-I, in some embodiments, a content-addressable storage server cloud 510 and/or interconnected set of content-addressable storage servers 520-522 may serve the function or provide storage for more general XDS systems. Whereas XDS-I emphasized support for images, and in particular medical images, the XDS protocol applies broadly to document storage, querying, and retrieval. Generally, an XDS Document Source may provide and register documents to an XDS Document Repository. The document repository may register stored documents in an XDS Document Registry. An XDS Document Consumer may query the XDS Document Registry in order to determine the locations of or references to documents. Once the XDS Document Consumer has received a response regarding location from the XDS Document Registry, it may retrieve the documents from the XDS Document Repository. Queries from the XDS Document Consumer to the XDS Document Registry may include patient identification as part of the query. An XDS Patient Identity Source may provide normalizing information for patient identity to be used in queries on the XDS Document Registry. The XDS Patient Identity Source may provide a normalized identifier for a single person or patient across multiple hospitals, multiple systems, and the like. This is discussed more below.

Building on the discussion above of FIG. 5, in some embodiments, device manager module 541, since it may provide the functions of searching for documents and retrieving documents, may act as both an XDS Document Registry and an XDS Document Repository. For example, in XDS Document Consumer may query device manager module 541, acting as an XDS Document Registry, for the location of the document, not pictured in FIG. 5. The device manager module 541 may then return a list of relevant documents stored in the cloud 510 to the XDS Document Consumer. The XDS Document Consumer may then request some or all of the matching documents from the device manager module 541, which would then be acting as the XDS Document Repository. The device manager module 541 could then retrieve the documents from the cloud 510.

In some embodiments, device manager module 541 may serve as an XDS Document Registry in cloud 510 and/or a single content-addressable storage server 520-522 or the cloud 510 may serve as the XDS document repository. If an XDS Document Consumer requested the location of an XDS document from the device manager module 541, acting as an XDS Document Registry, may return the location of the requested document. The XDS Document Consumer may then request the document from the cloud 510, or an individual content-addressable storage server 520-522, acting as an XDS Document Repository.

In any of these embodiments, an XDS Patient Identity Source may be implemented as part of any appropriate module or system, such as device manager module 541 or a combination of multiple device manager modules 541. In some embodiments, the XDS Patient Identity Source is implemented as part of cloud 510. Wherever it is implemented, in various embodiments, an XDS Patient Identity Source may provide a master patient index among numerous hospitals, doctors' offices, and the like. The XDS Patient Identity Source may include a database, data structure, or other data storage, with a unique identifier for each patient, and association from that unique identifier to the identifiers from multiple independent hospital information systems and/or other systems.

For example, one hospital information system may identify patients by Social Security number. Another hospital may identify patients by name. Yet other hospitals may identify patients by an identifier generated at the hospital. The master patient index, running as part of device manager module 541, cloud 510, etc. in FIG. 1 (or as part of any other application, device manager module, CAS server, CAS cloud, or as a separate application), may store a single unique identifier for the patient and associations from that single unique identifier to each of the identifiers from the various hospital information systems. Therefore, for example, a single patient John Smith may have a single unique identifier in system 500. This single unique identifier may be associated with his Social Security number at a first hospital information system, his name for a second hospital information system, and the hospital—generated identifier for a third hospital information system. Therefore, when a request is received for information related to John Smith, that request can be associated with his single unique identifier and his single unique identifier can be used, in conjunction with its relationship with the other you identifiers, to query for and retrieve data related to John Smith from the multiple hospital information systems, each of which may have data stored in the cloud 510 (or elsewhere).

Virtual Packages

Traditionally PACS machines or other devices that manage medical images allow users to select files to write to a CD or DVD. Embodiments herein provide this functionality. In addition, certain embodiments herein will also allow a user to produce a virtual package (or "virtual disk," "virtual DVD," "virtual file grouping," etc.). The term "virtual package" as used herein is a broad term encompassing its plain and ordinary meaning including, but not limited to, a grouping or set of files, pointers to files, or other indicators of files. A virtual package may also refer to a single file including two or more subsections containing images, reports, or other medical data. Various embodiments herein allow a user to select a set of files to store in a virtual package. The system finds those files, and any related data, and subsequently stores them in a CAS server or cloud. The system then provides the user with an indication of the virtual package or the files in the virtual package (e.g., a GUID, set of GUIDs, etc.). Optionally, access control may also be included in the original request for the virtual package. That is, the user may be able to specify what users or groups of users are allowed to access all files within the virtual package (or perhaps a subset of files in the virtual package) and the content-addressable storage server or CAS cloud will then control access based on that information.

Figure 7:
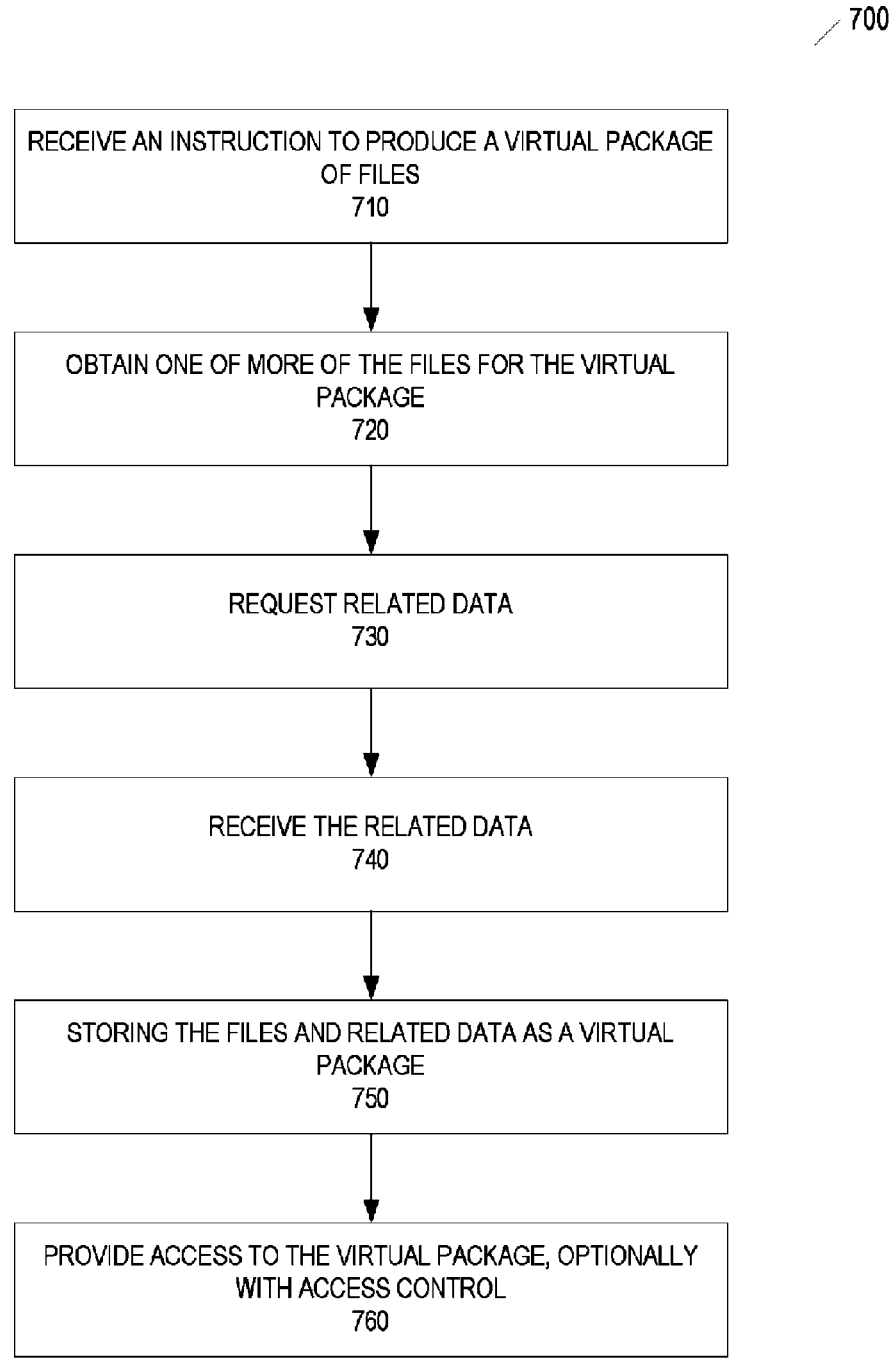
FIG. 7 is a block diagram representing an exemplary process for creating and managing virtual packages.

FIG. 7 illustrates an exemplary process for creating and managing virtual packages. In block 710, an instruction is received to produce a virtual package. This instruction may be received at a computer or server via a programmatic interface, for example, as an XML or other structured file received via a web service. The instruction to produce a virtual package may also be received via a web page or other interface where a user can select files via drop down boxes, radio boxes, selection boxes, or other mechanisms. For example, a user at a PACS machine running an embodiment would be able to select files to include in a virtual package (via a web-based selection menu, e.g.).

In some embodiments, a shared archive module or other program may allow a user to select files in the shared archive to include in a virtual package as part of block 710. Shared archives are discussed elsewhere herein. The files selected may be images, reports, or any other type of data. For example, a user may select all of the reports related to a particular patient or a particular study, series, or SOP. The user may also select all of the files related to a particular accession number. The term "SOP," as used herein is a broad term, encompassing its plain and ordinary meaning, including, but not limited to a "service object pair" in DICOM.

In block 720, the files indicated by the user for inclusion in the virtual package are obtained. In some cases, these files may be stored locally to the PACS machine or other software that received the instruction to produce the virtual package in block 710. In other embodiments, a subset of the files may be stored locally. As such, a request may be sent to a different computer or server to obtain one or more of the files to be included in the virtual package. This request may be sent to a different PACS machine, a CAS server or cloud, a database, or any other appropriate storage location. Obtaining the files may include reading the files from a global storage system, such as CAS server or cloud. In yet other embodiments, obtaining these files may include obtaining the files from the original request to produce a virtual package. For example, one or more of the files may be attached to the request to produce the virtual package received in block 710. More specifically, if a user at an application were to select a number of images and reports related to an accession number and attached a few of those files to the request that is received in block 710, then obtaining the one or more files may include retrieving those files attached to the original request in addition to obtaining some of the files locally and/or from a global storage system, such as a CAS cloud. The files to include in the virtual package may also come from other locations as noted herein.

In various embodiments, the user may also request inclusion of related data the virtual package. The related data is requested in block 730. For example, if a user were to select files related to an accession number, the user may also request that any data related to that accession number be included in the virtual package. This may be useful, for example, in cases in which a user wants to include all available data related to an accession number, patient, study, or other grouping, in one virtual package so that subsequent users of the virtual package may have easy access to all of the related files. Requesting related data can be very complex, as discussed elsewhere herein.

As noted elsewhere herein, communicating to another system to find related data may also require translating an identifier using a master patient index. The master patient index may provide a single identifier for each patient across multiple systems. Using the master patient index to query for related data may include sending the master patient index along with the request for related data or it may include translating to the destination system's patient index via the master patient index. For example, if a master patient index is being used and system A is requesting from system B related data for a patient, then system A may have to convert its patient identifier into the master patient index and from there obtain the patient index used in system B. Similar structures and techniques may be used for other unique identifiers or other identifiers such as accession number, study number, series number, and SOP number.

In some embodiments, requesting related data may include requesting data related to information that was received in the instruction in block 710, such as accession number or patient number, or it may include retrieving data from one or more of the files to be included in the package and using that data to request related data. For example, if a package is being created for a patient that should include all of the files related to that patient, then the original request received in block 710 may be used in order to identify the patient. Additionally, once files are obtained for that patient, accession numbers, study numbers, series numbers, SOP numbers, and the like may be extracted from one or more of those files and requests may be made for the data related to those accession numbers, series numbers, study numbers, and/or SOP numbers.

In block 740, the requested related data is received. In addition, in block 740 other related data may also be received even if it was not specifically requested. For example, receiving the related data may include receiving an HL7 broadcast message. The HL7 messages may include patient related information and that patient related information may be matched to local patient information. For example, a PACS machine may have studies or X-rays related to a patient. An HL7 message may be broadcast by another system that has related reports, other images, follow on images, etc. That incoming message may be matched by the patient-related information, as discussed elsewhere herein. In some embodiments, the related data is included in the HL7 message itself. In other embodiments, the HL7 message may not include the related data but may indicate the source from which related data can be received. In such embodiments, the related data may be requested from the machine or system that broadcast the HL7 message. After that data is requested, it may be received by the requestor.

In some embodiments, the related data may be retrieved using DICOM query and retrieve based on accession number as part of block 740 and/or block 730. For example, if there is a DICOM server that has related data and a system would like to request and receive that related data, the system may send a DICOM query/retrieve based on the accession number. In other embodiments, the system may send the DICOM server a request for a modality worklist and match to that modality worklist and from there a query based on the matches in the modality worklist. Receiving the data may also include receiving and reading a DICOM Structured Report that came with various images. This DICOM Structured Report may be broadcast or otherwise sent to the receiving system with or without first querying for it. A DICOM Structured Report may be requested based on accession number, patient number, study number, series number or SOP number. In yet other embodiments, an HTTP request may be sent to a PACS server or other source and a web page, structured document, or the like may be received in response. This web page or structured document may be parsed to extract related data to be used in subsequent blocks of method 700. Related data may also be retrieved from a database using stored procedures and/or SQL queries.

In some embodiments, when files and related data are received in block 740, then that data is parsed and put in a canonical format so that it may be stored in a coherent fashion in the virtual package. For example, receiving a DICOM Structured Report may be followed by parsing the DICOM Structured Report and storing the data in the database. Similarly, if a plain text file is received after a query for related data, then that plain text file may be parsed and stored in a database. Subsequently, all of the related data stored in the database may be output in XML or another format in order to store it as part of the virtual package. In various embodiments, the format to which the related data or obtained files are converted may be DICOM or some other format such as a human readable format that is either standard, indicated in a configuration file, or chosen by the user as part of the instructions to produce the virtual package.

In block 750, the files and the related data are stored as a virtual package. A virtual package may take many forms. For example, the files and related data obtained in earlier blocks may be stored individually in a content-addressable storage server. Upon storage of each of these files, a GUID or other identifier may be returned. These GUIDs may then be used as identifiers inside the virtual package. A user of the virtual package may be able to retrieve the files in the virtual package based on the GUIDs. In other embodiments, all of the files may be stored locally grouped together as a single file (for example, as a tar ball or other grouping). This single file may be stored in the CAS server or cloud, at which time a single GUID may be returned. The single stored file may also include metadata indicating the location identification and other pertinent information related to each of the individual files stored therein. In some embodiments, each individual file is stored in the CAS server or cloud as described above and subsequently a merge is requested in which all of the individual CAS files are merged together as a single CAS file and, optionally, the individual files are deleted from the CAS. In this way, the CAS server or cloud provides a GUID for the combination of all of the files together. This procedure may also include creating and/or maintaining the metadata as described above for the stored virtual package. Storing the individual files and/or the single file in the CAS may also be accompanied by keeping history data, auditing, and other information. For example, a file may be created or a log stored that indicates who created the virtual package, when they created it, its size, its contents, etc. This may be the case whether each file is stored separately and those individual files are used as the package, a single file is stored after being grouped together, or whether the files are merged in the CAS.

In some embodiments, access control information is also provided to the CAS. The access control information may include email addresses, user names, or other identifiers to indicate what individuals, what login accounts, what groups of people, or other groupings or individuals (for example, such as systems) should have access to either individual files in the virtual package or to the virtual package itself. As such, when access is provided in block 760 to the virtual package the access to that package may be controlled. For example, if access control information is included for a virtual package, then a user who has access to that package may receive an email indicating that the package has been stored in the CAS server or cloud and that that user may have access to it at that point. In other embodiments, the user may have to subscribe to an event notification in order to receive that email, as described elsewhere herein. That user may be able to log into or otherwise authenticate to the CAS server or cloud in order to access the virtual package. When attempting to access the virtual package, the access control of that user may be checked and only when that user has appropriate permissions may the user access, modify, delete, or perform other actions on either the individual files in the individual package or the virtual package as a whole.

In some embodiments, other types of access control can also be provided by a CAS server, a CAS cloud, or other global storage system. For example, access to a particular patient, series, study, or accession number may be turned off for all users. This may be useful, for example, if there is an issue with a patient, such as pending malpractice litigation for that patient. In other embodiments, an individual user's access may be denied for all data in the global storage system. For example, if an administrator or other employee was fired then one precaution for the data in the CAS cloud may be to deny that person's account access to any data in the CAS regardless of previous permission. Controlling access in this way may be performed as part of a CAS server, CAS cloud, a separate application, or in any other appropriate manner.

Turning to FIGS. 1 and 7, an application 132 may receive a request to produce a virtual package in block 710. Some of the files in the request may be attached to the request, other files may be stored locally in application 132, and additional files for the virtual package may be stored elsewhere. Application 132 may obtain those locally stored files and other files either from the local disk, from the CAS cloud 110, or from the other sources (not pictured). The application may then send a request for related data to the CAS cloud 110, a PACS application 131, and/or to a shared archive module 133. Each of those systems or devices may respond with related data in various formats. The application 132 may then store the related data as a virtual package in the CAS cloud 110, using the various techniques and embodiments described above. The user of the application may have also provided access control information for the virtual package. Thereafter, the CAS cloud 110 may control access to the virtual package requested and produced previously as part of block 760.

Various embodiments herein provide for the creation and accessing of virtual packages. When a user would like to create a collection of data that might traditionally be put on the disk, the user may not necessarily want to actually produce a physical disk. Therefore, embodiments herein allow the user to create a virtual package (perhaps called a "virtual disk"). The virtual package may be more easily distributed because it is not limited to physical disks. Further, as discussed herein, access can be finely controlled with a virtual package and updated over time in ways that are difficult or impossible with physical disks.

Additional Embodiments of Virtual Packages

This section provides more examples of virtual packages, their creation, and access. The contents of the virtual package could be, for example, from the CAS cloud 110. If a user is working at a PACS server 131, the user may be able to create a virtual package. The virtual package may include a number of objects, such as X-rays or MRIs, associated with a particular patient or group of patients. The PACS server 131 may communicate with the device manager module 141 and request the GUIDs for the objects in the virtual package. The device manager module 141 may then look in the GUID/object database 151 in order to determine the objects' associated GUIDs. The virtual package may simply be a collection of GUIDs.

Figure 10:
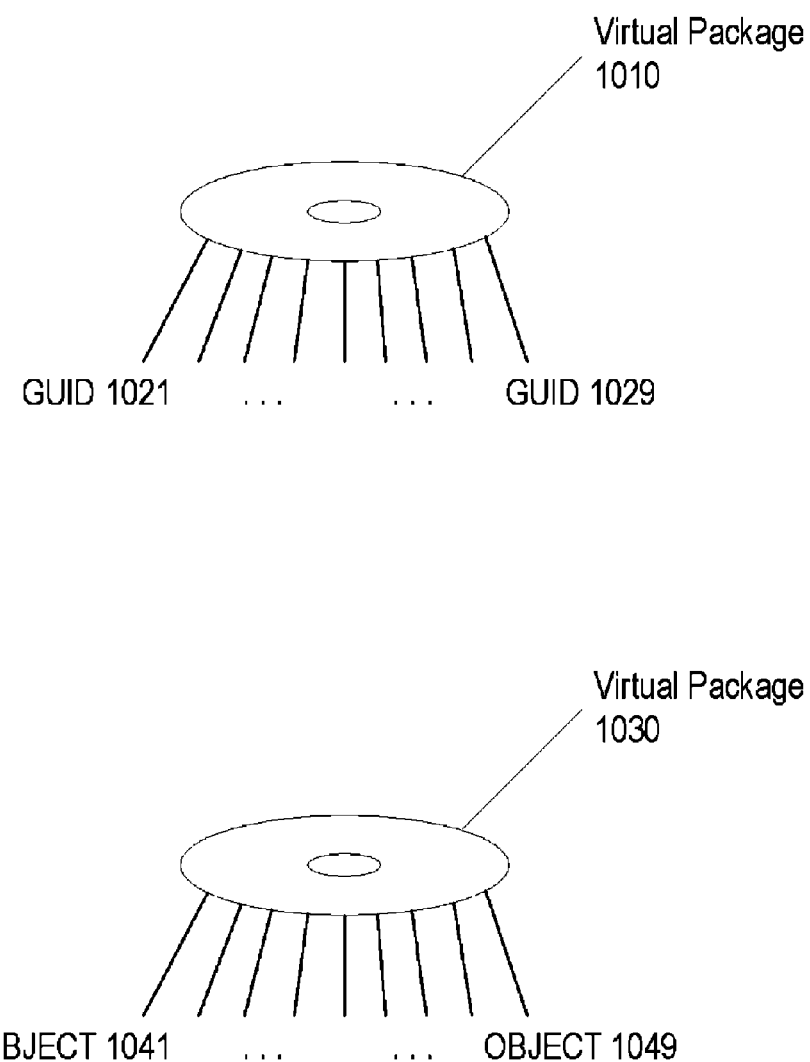
FIG. 10 illustrates abstract representations of virtual packages.

When that same user or another user accesses the PACS server 131, or perhaps a different PACS server, in order to retrieve the virtual package, the PACS server 131 may communicate with the device manager module 141 in order to retrieve all of the objects associated with the GUIDs that are associated with the virtual package. An abstract representation of the virtual package is given in FIG. 10. In FIG. 10, a virtual package 1010 is associated with multiple GUIDs 1021-1029. When a user later attempts to access virtual package 1010 from the PACS server 131, the PACS server 131 will access the stored representation of the virtual package 1010 in order to obtain an indication of which GUIDs are associated with virtual package 1010. The PACS server 131 will then retrieve the objects associated with each GUID. Together, these objects make up the content of the virtual package. The user will then be able to view, modify, or perform any other action on the virtual package, including, if appropriate, burning a physical disk based on the virtual package.

In some embodiments, virtual packages will include references to objects instead of GUIDs. Referring again to FIG. 10, a virtual package 1030 maintains references to various included objects references 1041-1049. When a user later attempts to retrieve virtual packages 1030, the application module will ask for the various objects from the underlying filesystem, such as the device manager module 141 in FIG. 1. The device manager module 141 may then look in its own database 151 in order to determine what GUIDs are associated with each of the object references. Once the device manager module 141 has the GUIDs for the object references 1041-1049, it can request the objects associated with the determined GUIDs from the content-addressable storage cloud 110. The content-addressable storage cloud 110 may then return the objects associated with the GUIDs to the device manager module 141. The device manager module 141 may then return the objects associated with the GUIDs, which are in turn associated with the object references 1041-1049, to the requesting application module. The requesting application module would then have access to the contents of the virtual package.

Accessing a Virtual Package after Creation

Figure 9:
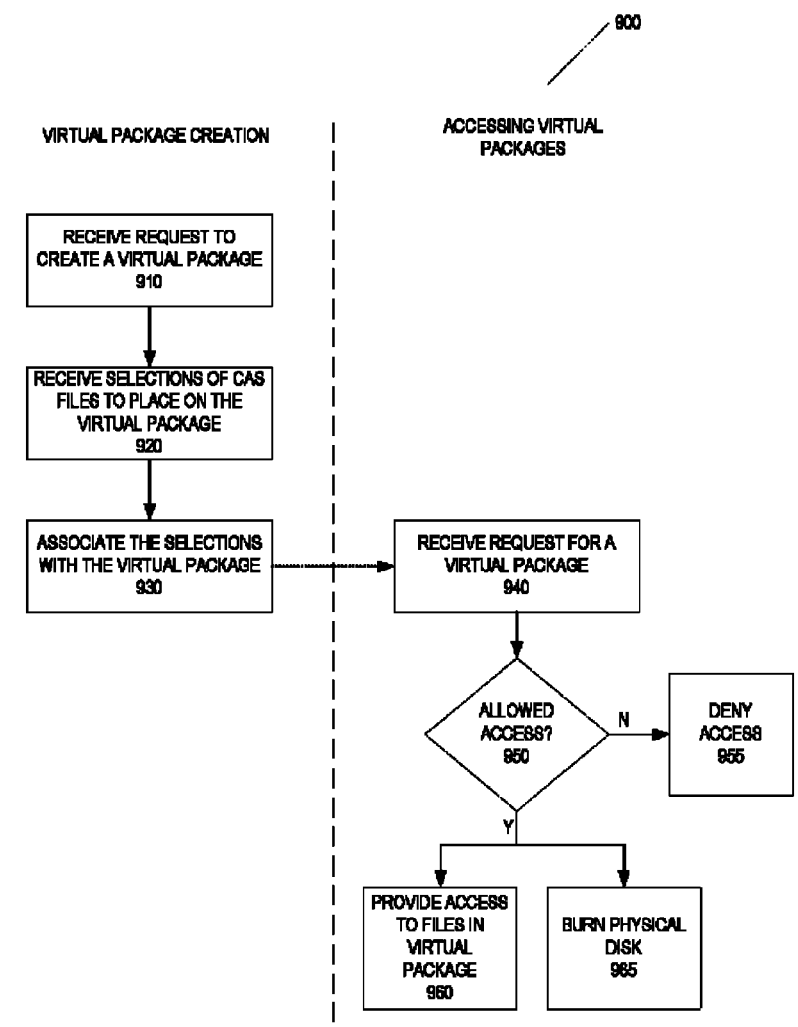
FIG. 9 is a block diagram representing an exemplary process for virtual package management in a system of interconnected content-addressable storage systems.

FIG. 9 is a block diagram illustrating a method 900 for creating and accessing virtual packages. Generally, in some embodiments, the virtual package may be created and associated with numerous files in the content-addressable storage system. After the disk is created, access to that disk may be provided only to those who are allowed access. Further, physical disks may be burned based on virtual packages.

In block 910, a request for virtual package may be received. The request for the virtual package may come from a user using an application module, such as an application module 131 or 132, as depicted in FIG. 1. The request to create the virtual package may be received at the device manager module 141 or 142, as depicted in FIG. 1. In some embodiments, a content-addressable storage server 121-125 in the cloud 110 may be responsible for creating virtual packages. The request to create a virtual package may also include, depicted as block 920, a selection of files to be placed on the virtual package. The selection of files may be stored locally at the receiver, such as device manager module 141 or 142, or they may be stored on the content-addressable storage servers in the cloud 110. The selection of files may also include related data, as discussed elsewhere herein.

In block 930, the selections of files are associated with virtual package. The virtual package may be associated with an identification number, which may be stored in a database or other file, such as database 151 or 152 in FIG. 1. Associating the files with the virtual package may include associating identifiers associated with each of the files to the identification number associated with the virtual package. As depicted in FIG. 10, a virtual package 1010 may be associated with identifiers 1021-1029, and the identifiers for the files, when the files are stored in the content-addressable storage cloud 110, may be GUIDs 1021-1029.

At some point after the creation of one or more virtual packages, the application managing virtual packages may receive a request for a particular virtual package, in block 940. The request to access a particular virtual package may be a request that identifies the virtual package by an identification number. In some embodiments, such as that depicted in FIG. 9, when a request for virtual package is received, the application may determine in block 950 whether the requester is allowed to access the virtual package. If access is not allowed, then in block 955, access is denied to the requester. If access is allowed, as determined in block 950, then the requester is given access to the virtual package and may access files in the virtual package as part of block 960, burn a physical disk related to the virtual package in block 965, or perform any other appropriate action.

Looking to the example of FIG. 1, if a device manager module 141 is managing virtual packages, then when someone using application module 131 requests the virtual package, assuming that the requester is allowed access, the device manager module 141 may look up that virtual package and its associated objects in the database 151. The virtual package may be associated with a number of GUIDs, which represent the objects or data files in the virtual package. When the requester attempts to access the files in the virtual package, the device manager module 141 may request those files using the GUIDs from content-addressable storage server 121. As described herein, if the content-addressable storage server 121 does not have the data files stored locally, then it may request those data files from other CAS servers in the cloud 110.

Access Control

In various embodiments, access control may also be provided by the content-addressable storage servers in the cloud 110. Access control may fall into various categories, such as role-based access control and user-based access control. Typically, role-based access control will require a user to login and that user will be associated with the role. The access that the user has to the data may be defined by a role. User-based access control is similar in that a user must login and that user will have access to the data based on his or her specific access profile. In various embodiments, the access control mechanisms may control reading data, writing data, modifying data, deleting data, etc. Access control may be defined for individual objects, such as X-rays for particular patients, or for types of objects or groups of objects. For example a given user may have access to all of the medical images for a particular hospital and may not have access to medical images for any other hospital (even if the other hospitals also have data stored in the cloud). On the other hand, a clinical research organization's analyst may have access to diagnostic results for a number of different hospitals, but may not have access to any information that personally identifies any of the patient's with whom the results are associated.

In some embodiments, when either a user or a computer system attempts to access something in the content-addressable storage cloud 110, authentication information may be required. As used herein, authentication information may be a username and password, an identifier, an RFID chip read by a device coupled to the system, or any other authentication mechanism or technique known to those skilled in the art. For example, a username and password may provide authentication to access the cloud 110. If the username and password do not match or otherwise fail, then access to the cloud 110 may be denied.

In some embodiments, GUIDs associated with objects stored in the cloud 110 may also be associated with a group number. Additionally, particular usernames and passwords may be associated with one or more group numbers. As such, when a particular user logs in using a username and password that particular user may have access to only the objects associated with the group numbers to which it has access. For example, consider a scenario in which multiple hospitals are all using the same cloud 110 to store their patient data. Each hospital may be associated with the group number. Each hospital may also have a username and password that users or computer systems associated with that hospital may use in order to access data. By providing this kind of differentiated access control, the content-addressable storage system may effectively isolate the patient files for one hospital from those of another hospital. Such an arrangement may provide certain benefits. By allowing multiple hospitals to store a patient data on the same cloud, each hospital may not necessarily have to build or support the physical computing and communication infrastructure needed to support the cloud. The infrastructure may be provided by one of the hospitals or it may be provided by a third-party. Either way, economies of scale may apply and the storage of data on this cloud from multiple hospitals may provide monetary and other benefits.

Figure 11:
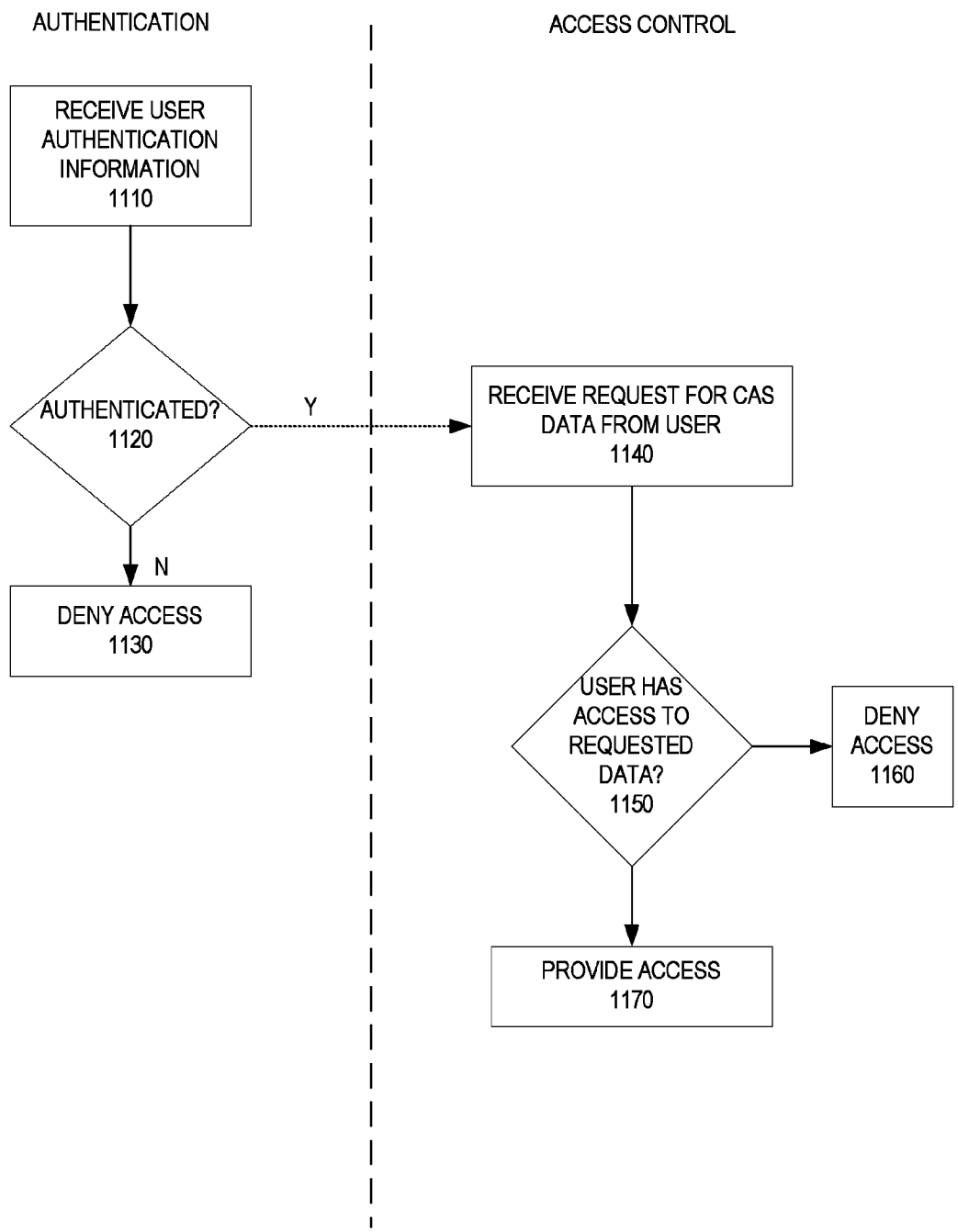
FIG. 11 is a block diagram representing an exemplary process for access control in a system of interconnected content-addressable storage systems.

FIG. 11 depicts a process for providing access control in a cloud of interconnected content-addressable storage servers. In block 1110, user authentication information is received. The user authentication information may be a username and password or other identifying or authenticating information. In block 1120, a check is made to determine whether the user authentication information is valid. This can include determining whether the username and password received from a user is valid, or checking authentication with any other known method. If the user is not authenticated, then access to the system is denied in block 1130. If the user is authenticated, as determined in block 1120, then thereafter the system may receive a request from the user for stored data in block 1140. That request may come in the form of a request for a particular GUID. Even though the user has already been authenticated, the user may not have access to all of the data stored in the content-addressable storage cloud, such as cloud 110. As such, in block 1150, a check is made to determine whether the user has permission to access the requested data. Checking whether the user has access to the requested data may take a number of forms. For example, in role-based access control, a determination may be made to see whether a role associated with the user, such as the role of analyst or administrator, provides that user with access to the requested data. Access control may also be finer grained. For example, access to files may be determined on a per user basis. As such, a check may be made to determine whether the user is allowed to access the particular file. If the user does not have permission to access the requested data, then access will be denied in block 1160. If the user does have permission to access the data, then in block 1170 access is provided.

Returning to FIG. 1, if a user is using a shared archive module 133 and attempts to access a file, such as an X-ray, that is stored in the cloud 110, then the shared archive module 133 will request that file from the shared archive CAS module 143. The shared archive CAS module 143 will attempt to retrieve the file from the cloud 110. In some embodiments, the device manager module will check the access control information for the user. In other embodiments, the shared archive CAS module 143 will provide authentication information for the user to the cloud 110, and a content-addressable storage server 123 will check to see whether the user has proper authentication to access the requested file. If the user does have access to the requested file, then the cloud 110 will return the file to the shared archive CAS module 143, and the shared archive CAS module 143 will send the file to the shared archive module 133.

Interfaces for an Interconnected Content-Addressable Storage System

In some embodiments, content-addressable storage servers in the cloud 110 provide entities communicating with content-addressable storage servers interfaces that are similar to those normally associated with file systems. For example, in some embodiments, a CIFS interface is provided by the content-addressable storage servers in the cloud 110. Therefore, a program that is written to communicate with the familiar CIFS interface will be able to access the content-addressable storage servers. In other embodiments, other interfaces are provided, such as WFC interfaces. IHE Cross Enterprise Document Sharing (XDS) interfaces are provided in some embodiments. Additionally, some embodiments herein may be used as an XDS Document Repository, document registry, document source, or document consumer. One of the advantages of providing a familiar interface is that it will allow a program written to work with the familiar interface, even if the underlying storage is different, to work with little or no modification.

Returning again to the CIFS interface, the interface may act as a filter on requests for stored files. When a request for a file is sent to the file system manager, the file system manager will check to see whether the file is stored locally in whole or in part, and if it is not, then it will be requested via a CIFS call. The requested file will then be retrieved from a remote location, and sent to the requester.

Figure 12:
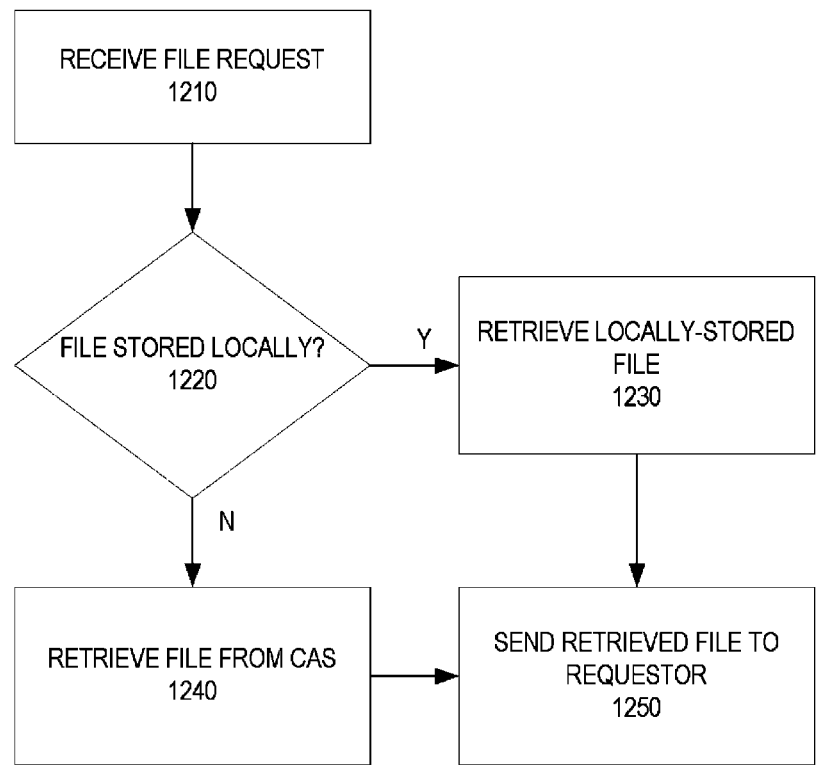
FIG. 12 is a block diagram representing an exemplary process for providing a file system interface in a system of interconnected content-addressable storage systems.

As another example, consider the method depicted in FIG. 12. A file request is received in block 1210. A check is made to determine whether the file is stored locally, in whole or in part in block 1220. If the file is stored locally, then in block 1230 the locally stored file is retrieved. Subsequently, the retrieved file is sent to the requester in block 1250. If, however, it is determined in block 1220 that the file is not stored locally, then the file is retrieved from the content-addressable storage server in block 1240. Examples of retrieving files from a content-addressable storage server are presented elsewhere herein. The retrieved file is then sent to the requester as part of block 1250.

There may be advantages to embodiments such as those depicted in FIG. 12. For example, systems requesting files do not need to know whether the file is stored locally or stored remotely in the content-addressable storage server. As such, in some embodiments, the management of the stored data is independent of the representation shown to the end-user. As such, the end-user, such as an application module 131, can operate independently of the CAS mechanisms and independent of any changes to the underlying file storage system. Therefore, in some embodiments, the content-addressable storage system as a whole may be modified or updated without requiring any modifications or updates to an application module 131 that may rely on the storage capabilities of the content-addressable storage system.

Encryption for Transmission

The encryption protection provided in various embodiments may be manifold. Data may be encrypted as it is sent from one content-addressable storage server to another. It may also be encrypted while it is stored in the content-addressable storage server. Each of these provides a different kind of protection. Encryption during transmission of data will help protect the data from being "snooped" on the transmission line or read by programs or individuals. Encryption during storage, on the other hand, will protect against the data being readily readable in the case that someone is attempting to read what is stored on the content-addressable storage server. Each of these two types of data protection is important for HIPAA.

Various embodiments herein provide for encrypted transmission between both an application, such as an application module 131, and a content-addressable CAS server, such as content-addressable CAS server 121, as well as among various content-addressable CAS servers, such as those in the cloud 110. Encryption works, generally, by taking unencrypted data and combining it with or modifying it based on a cipher. The encrypted data can then only be read by decrypting the data using a key corresponding to the cipher. Various embodiments of encryption are known to those skilled in the art.

The system 100 of FIG. 1 may use encryption over one or more of the communication paths within the system 100. For example, data transferred between or among content-addressable storage servers in the cloud 110 may be encrypted. The encryption may be transmission encryption, such as that supported by secure socket layers (SSL) and secure hypertext transfer protocol (HTTPS). Such encrypted transmission will allow a transmitting entity to send unencrypted data to another entity without separately encrypting the data before the transmission. The encryption is handled by the transmission protocol in these cases. On the other hand, and possibly in combination with encrypted transmission, data can be encrypted before it is sent. In such a case, the receiving entity may have the key or token associated with the cipher that was used to encrypt the data on the sender's side.

As another example, consider embodiments in which a data object, such as an X-ray, is being stored to the cloud 110 by an application module 131. The application module 131 may send the data object to the device manager module 141, possibly using encryption. The device manager module may then send, possibly using encryption, the object into the content-addressable storage cloud 110. In doing so, the content-addressable storage cloud 110 will return a GUID associated with the object. The device manager module will then store the GUID in its GUID/object database 151.

Considering the example system shown in FIG. 1, when the device manager module 141 first send the object, possibly using encryption, in the content-addressable storage cloud 110 it will first go to a particular content-addressable storage server 121. Content-addressable storage server 121 will at first store the object locally in its own storage. After some predetermined amount of time or once its data storage capacity is reaching a certain predefined threshold, such as 50%, 80%, or 90%, certain amounts of data will be offloaded and sent to other content-addressable storage servers in the cloud 110, such as content-addressable storage server 123. In order to send the object from one content-addressable storage server to another, certain embodiments herein will first encrypt the object.

In some embodiments, encryption may be performed using data encryption standard (DES) or advanced encryption standard (AES) algorithms. Encryption may be performed by the content-addressable storage server 121 or by any other appropriate computing device. The content-addressable storage server 121 may also determine certain file trailer or other metadata, such as a checksum or a digest, such as an MD5 digest. This file trailer or other metadata may be then sent to the same content-addressable storage server to which the object is being offloaded. The receiving content-addressable storage server 123 may then use the file trailer or other metadata in order to determine whether the received object has been received correctly. If the received object has been received correctly, then, in some embodiments, acknowledgments of this fact may be sent back to be sending content-addressable storage server 121. If, however, the received object has not been received correctly then, in some embodiments, a request may be sent back to the sending content-addressable storage server 121 to resend the object. The encryption of the objects when data is sent from one content-addressable storage server 121 to another 123 may help provide safety and security of patient data as it is in transit.

In some embodiments, objects and other data are encrypted when sent between any two entities, such as between the content-addressable storage server 121 and the device manager module 141, and/or between a device manager module 141 and an application module 131.

FIG. 13 depicts an example process for transmitting data using encryption. In block 1310, a request is received to transfer a file. The file may be encrypted in block 1320, and the encrypted file may be transferred in block 1330. Encryption and transfer of data are described elsewhere herein. The receiver may receive the file in block 1340 and decrypt the file in block 1350. Decryption of data is described elsewhere herein. As described above, a checksum or other data check may also be applied to the data to ensure the integrity of the received data. In performing a process such as that depicted in FIG. 13, an unencrypted file may be received at a receiver, without that file ever being in transit in an unencrypted state.

Additional Embodiments

The processes and systems described herein may be performed on or encompass various types of hardware, such as computer devices, such as computer systems. In some embodiments, application modules 131-133, XDS-I modules 531, 560, and 570, or the machines running application modules 131-133, XDS-I modules 531, 560, and 570, the device manager modules 141-143 or the machines running device manager modules 141-143, the databases 151-153, 551 or the machines running databases 151-153, 551, and the CAS servers, e.g. 121-125, 520-522, in clouds 110, 510 may be each be separate devices, applications, or processes or may run as part of the same devices, applications, or processes—or one of more may be combined to run as part of one application or process—and/or each or one or more may be part of or run on a computer system. A computer device or system may include a bus or other communication mechanism for communicating information, and a processor coupled with the bus for processing information. The computer devices or systems may have a main memory, such as a random access memory or other dynamic storage device, coupled to the bus. The main memory may be used to store instructions and temporary variables. The computing devices or systems may also include a read-only memory or other static storage device coupled to the bus for storing static information and instructions. The computer systems may also be coupled to a display, such as a CRT or LCD monitor. Input devices may also be coupled to the computer system. These input devices may include a mouse, a trackball, or cursor direction keys.

Each computing device may be implemented using one or more physical computers, processors, embedded devices, field programmable gate arrays (FPGAs) or computer systems or a combination or portions thereof. The instructions executed by the computing device may also be read in from a computer-readable medium. The computer-readable medium may be non-transitory, such as a CD, DVD, optical or magnetic disk, flash memory, laserdisc, carrier wave, or any other medium that is readable by the computing device. In some embodiments, hardwired circuitry may be used in place of or in combination with software instructions executed by the processor. Communication among modules, systems, devices, and elements may be over a direct or switched connections, and wired or wireless networks or connections, via directly connected wires, or any other appropriate communication mechanism. Transmission of information may be performed on the hardware layer using any appropriate system, device, or protocol, including those related to or utilizing Firewire, PCI, PCI express, CardBus, USB, CAN, SCSI, IDA, RS232, RS422, RS485, 802.11, etc. The communication among modules, systems, devices, and elements may include handshaking, notifications, coordination, encapsulation, encryption, headers, such as routing or error detecting headers, or any other appropriate communication protocol or attribute. Communication may also messages related to HTTP, HTTPS, FTP, TCP, IP, ebMS OASIS/ebXML, DICOM, DICOS, secure sockets, VPN, encrypted or unencrypted pipes, MIME, SMTP, MIME Multipart/Related Content-type, SQL, HL7 Version 2.5, HL7 Version 2.3.1, etc.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

Following this document are a number of other documents, appendices, figures, diagrams, and publications. Each of these is incorporated herein by this reference in its entirety and made a part of this specification.

What is claimed is:

1. A method for providing a shared archive in an interconnected content-addressable storage system, said method executing on one or more computing devices, said method comprising:
receiving a first indication to store a first file containing first medical data and first related metadata in a content-addressable storage cloud from a first computer implemented application;
parsing, using the one or more computing devices, first related metadata of the first file to produce first information, first information comprising at least one of the following:
a portion of a DICOM header;
patient name;
doctor;
time medical image was taken; and
hospital;
storing the first file in the content-addressable storage cloud;
receiving a first identifier for locating the stored first file;
storing the first information and first identifier in a shared archive and associating the first identifier and the first information with each other to facilitate searching of the shared archive;
receiving a second indication to store a second file containing second medical data and second related metadata in the content-addressable storage cloud from a second computer-implemented application;
parsing, using the one or more computing devices, second related metadata of the second file to produce second information, second information comprising at least one of the following:
a portion of a DICOM header;
patient name;
doctor;
time medical image was taken; and
hospital;
storing the second file in the content-addressable storage cloud;
receiving a second identifier for locating the stored second file;
storing the second information and second identifier in the shared archive and associating the second identifier and the second information with each other to facilitate searching of the shared archive;

receiving a first query from a requestor for a first data item and related data from the shared archive, the related data comprising medical images that are not directly responsive to the first query;

when the first information satisfies the first query related to the first data item and the second information fails to satisfy the first query related to the first data item:
determining a second data item based at least in part on the first data item, wherein the first data item and the second data item are distinct, the second data item comprising at least one of the following:
social security number;
accession number;
study number;
serried number;
patient identifier; and
hospital number; and
performing a second query for the second data item, thereby facilitating execution of the query requesting related data; and when the first information satisfies the first query related to the first data item and the second information satisfies the second query related to the second data item, responding to the requestor of the first query with information related to the first file and the second file.

2. The method of claim 1, wherein determining the second data item based at least in part on the first data item comprises determining the second data item based at least in part on the first information.

3. The method of claim 1, wherein the first data item is a patient name, and determining the second data item based at least in part on the first data item comprises determining the second data item based at least in part on a master patient index entry for the first data item, the master patient index comprising an index that associates other patient identifies such as social security numbers and alternative names, with the same patient.

4. The method of claim 1, wherein responding to said query with information related to the first file comprises responding to said query with the first identifier.

5. The method of claim 1, wherein responding to said query with information related to the first file comprises responding to said query with the first file.

6. The method of claim 1, wherein responding to said query with information related to the first file comprises responding to said query with the first information.

7. The method of claim 1, wherein responding to said query with information related to the first file only occurs when a requestor has proper access control permissions to receive the information related to the first file.

8. The method of claim 1, wherein parsing first related metadata of the first file to produce first information comprises parsing a DICOM header.

9. The method of claim 1, wherein parsing first related metadata of the first file to produce first information comprises parsing a DICOM Structured Report.

10. A system for providing a shared archive in an interconnected content-addressable storage system, said system comprising one or more computing devices configured to:
receive a first indication to store a first file containing first medical data and first related metadata in a content-addressable storage cloud from a first computer-implemented application;
parse first related metadata of the first file to produce first information;
store the first file in the content-addressable storage cloud;
receive a first identifier for locating the stored first file;
store the first information and first identifier in a shared archive;
receive a second indication to store a second file containing second medical data and second related metadata in the content-addressable storage cloud from a second computer-implemented application;
parse second related metadata of the second file to produce second information;
store the second file in the content-addressable storage cloud;
receive a second identifier for locating the stored second file;
store the second information and second identifier in the shared archive;
receive a first query from a requestor for a first data item and related data from the shared archive the, related data comprising medical images that are not directly responsive to the first query;
when the first information satisfies the first query related to the first data item and the second information fails to satisfy the first query related to the first data item:
determine a second data item based at least in part on the first data item, wherein the first data item and the second data item are distinct; and perform a second query for the second data item; and
when the first information satisfies the first query related to the first data item and the second information satisfies the second query related to the second data item, respond to the requestor of the first query with information related to the first file and the second file.

11. The system of claim 10, wherein determining the second data item based at least in part on the first data item comprises determining the second data item based at least in part on the first information.

12. The system of claim 10, wherein determining the second data item based at least in part on the first data item comprises determining the second data item based at least in part on a master index entry for the first data item.

13. The system of claim 10, wherein responding to said query with information related to the first file only occurs when a requestor has proper access control permissions to receive the information related to the first file.

14. The system of claim 10, wherein receiving the first indication to store the first file in the content-addressable storage cloud comprises mirroring a directory to which a copy of the file has been stored.

15. The system of claim 10, wherein receiving the first indication to store the first file in the content-addressable storage cloud comprises receiving the first file via a file system interface.

16. The system of claim 10, wherein receiving the first indication to store the first file in the content-addressable storage cloud comprises receiving the first file via a content-addressable storage interface.

17. A non-transient computer-readable medium comprising computer-executable instructions for providing a shared archive in an interconnected content-addressable storage system, said computer-executable instructions, when running on one or more computers, performing a method comprising:
receiving a first indication to store a first file containing first medical data and first related metadata in a content-addressable storage cloud from a first computer-implemented application;
parsing first related metadata of the first file to produce first information; storing
the first file in the content-addressable storage cloud;
receiving a first identifier for locating the stored first file;

storing the first information and first identifier in a shared archive;

receiving a second indication to store a second file containing second medical data and second related metadata in the content-addressable storage cloud from a second computer-implemented application;

parsing second related metadata of the second file to produce second information;

storing the second file in the content-addressable storage cloud;

receiving a second identifier for locating the stored second file;

storing the second information and second identifier in the shared archive;

receiving a first query from a requestor for a first data item and related data from the shared archive, the related data comprising medical images that are not directly responsive to the first query;

when the first information satisfies the first query related to the first data item and the second information fails to satisfy the first query related to the first data item:

determining a second data item based at least in part on the first data item, wherein the first data item and the second data item are distinct; and performing a second query for the second data item; and when the first information satisfies the first query related to the first data item and the second information satisfies the second query related to the second data item, responding to the requestor of the first query with information related to the first file and the second file.

18. The non-transient computer-readable medium of claim 17, wherein determining the second data item based at least in part on the first data item comprises determining the second data item based at least in part on the first information.

19. The non-transient computer-readable medium of claim 17, wherein determining the second data item based at least in part on the first data item comprises determining the second data item based at least in part on a master index entry for the first data item.

20. The non-transient computer-readable medium of claim 17, wherein responding to said query with information related to the first file only occurs when a requestor has proper access control permissions to receive the information related to the first file.

* * * * *